(12) United States Patent
Dooper et al.

(10) Patent No.: US 9,005,630 B2
(45) Date of Patent: Apr. 14, 2015

(54) FUSION PROTEINS FOR THE TREATMENT OF ALLERGIC DISEASES

(71) Applicant: Veterinaerinstituttet, Oslo (NO)

(72) Inventors: Maaike Maria Barbara Wilhelmina Dooper, Notteroy (NO); Bjarne Bogen, Snaroya (NO); Heidi Ragnhild Myrset, Fetsund (NO)

(73) Assignee: Veterinaerinstituttet, Oslo (NO)

( * ) Notice: Subject to any disclaimer, the term of this patent is extended or adjusted under 35 U.S.C. 154(b) by 0 days.

(21) Appl. No.: 13/666,023

(22) Filed: Nov. 1, 2012

(65) Prior Publication Data

US 2014/0120123 A1    May 1, 2014

(51) Int. Cl.
*A61K 39/00* (2006.01)
*C12N 9/96* (2006.01)
*C07K 14/75* (2006.01)
*C07K 14/435* (2006.01)

(52) U.S. Cl.
CPC ........... *C07K 14/75* (2013.01); *C07K 14/43509* (2013.01); *C07K 2319/01* (2013.01)

(58) Field of Classification Search
CPC ............. C07K 14/75; C07K 14/43509; C07K 2319/01
USPC ........................................ 424/185.1; 435/188
See application file for complete search history.

(56) References Cited

U.S. PATENT DOCUMENTS

| | | | |
|---|---|---|---|
| 6,403,089 B1 * | 6/2002 | Levy et al. ................ | 424/139.1 |
| 7,488,804 B2 | 2/2009 | Saxon | |
| 7,612,181 B2 * | 11/2009 | Wu et al. .................... | 530/387.3 |
| 7,632,495 B2 * | 12/2009 | Levy ........................... | 424/130.1 |
| 7,655,229 B2 | 2/2010 | Chan | |
| 2005/0164923 A1 | 7/2005 | Levy | |
| 2006/0078550 A1 * | 4/2006 | Levy et al. ................... | 424/94.2 |
| 2006/0171942 A1 | 8/2006 | Saxon | |
| 2007/0253948 A1 | 11/2007 | Chan | |
| 2009/0226435 A1 * | 9/2009 | Khare ........................ | 424/133.1 |
| 2010/0048486 A1 | 2/2010 | Levy | |
| 2010/0166802 A1 * | 7/2010 | Caplan et al. .............. | 424/257.1 |

FOREIGN PATENT DOCUMENTS

| | | |
|---|---|---|
| WO | 97/07218 | 2/1997 |
| WO | 2007/098934 | 9/2007 |

OTHER PUBLICATIONS

Shevatch. (Immunity. May 22, 2009;30:636-645).*
Shalev et al., (J Immunol. 2008;180:249-260).*
Motoyama et al., (J Agric. Food Chem. 2007;55(3).*
UniProt A2V732_9EUCA (Mar. 20, 2007) (Search results and sequence comparison available in SCORE).*

(Continued)

*Primary Examiner* — Cherie M Stanfield
(74) *Attorney, Agent, or Firm* — Tanya A. Arenson; Casimir Jones, S.C.

(57) ABSTRACT

The present invention relates to a fusion protein comprising a first peptide and a second peptide linked together with a linker, wherein the first peptide is an allergen and the second peptide is a targeting unit and the second targeting unit peptide is a FGL-2 C-terminal peptide according to SEQ ID no 1. Provided herein are also uses of said fusion protein as a vaccine for treating shrimp allergy, as well as a vaccine composition and methods of its production.

18 Claims, 21 Drawing Sheets

(56) References Cited

OTHER PUBLICATIONS

Figure 1:

Dooper et al., Modulation of human basophilic responses by a fibroleukin-allergen fusion protein, XXII World Allergy Congress, Cancun, Mexico, Dec. 4-8, 2011, pp. 1-25.

Liu Hao et al., The FGL2-FcgammaRIIB pathway: a novel mechanism leading to immunosuppression, European Journal of Immunology, Nov. 2008, vol. 38, No. 11, Nov. 2008, pp. 3114-3126.

Dimitrova, I., et al., Target silencing of disease-associated B-lymphocytes by chimeric molecules in SCID model of pristane-induced autoimmunity, Lupus, Basingstoke, GB, vol. 19, No. 11, Oct. 1, 2010, pp. 1261-1271.

Chan CW, Chan MW, Liu M, Fung L, Cole EH, Leibowitz JL, Marsden PA, Clark DA, Levy GA. Kinetic analysis of a unique direct prothrombinase, fgl2, and identification of a serine residue critical for the prothrombinase activity. Journal of immunology (Baltimore, Md : 1950) 2002; 168:5170-7.

Xie L, Ichimaru N, Morita M, Chen J, Zhu P, Wang J, Urbanellis P, Shalev I, Nagao S, Sugioka A, Zhong L, Nonomura N, Takahara S, Levy GA, Li X-K. Identification of a novel biomarker gene set with sensitivity and specificity for distinguishing between allograft rejection and tolerance. Liver Transplantation 2012; 18:444-54.

Turner H, Kinet JP. Signalling through the high-affinity IgE receptor Fc epsilonRI. Nature 1999; 402:B24-30.

Cassard L, Jönsson F, Arnaud S, Daëron M. Fcγ Receptors Inhibit Mouse and Human Basophil Activation. The Journal of Immunology 2012; 189:2995-3006.

Lehmann B, Schwab I, Böhm S, Lux A, Biburger M, Nimmerjahn F. FcγRIIB: a modulator of cell activation and humoral tolerance. Expert Review of Clinical Immunology 2012; 8:243-54.

Chu SY, Horton HM, Pong E, Leung IWL, Chen H, Nguyen D-H, Bautista C, Muchhal US, Bernett MJ, Moore GL, Szymkowski DE, Desjarlais JR. Reduction of total IgE by targeted coengagement of IgE B-cell receptor and FcγRIIb with Fc-engineered antibody. Journal of Allergy and Clinical Immunology 2012; 129:1102-15.

Gamez C, Sanchez-Garcia S, Ibanez MD, Lopez R, Aguado E, Lopez E, Sastre B, Sastre J, del Pozo V. Tropomyosin IgE-positive results are a good predictor of shrimp allergy. Allergy 2011; 66:1375-83.

Le Gall F, Reusch U, Little M, Kipriyanov SM. Effect of linker sequences between the antibody variable domains on the formation, stability and biological activity of a bispecific tandem diabody. Protein engineering, design & selection : PEDS 2004; 17:357-66.

* cited by examiner

A.

CP

B.

```
  1 MGHHHHHHHH HHSSGHIDDD DKGDALRFNK HYNHDLKFFT TPDKDNDRYP SGNCGLYYSS
 61 GWWFDACLSA NLNGKYYHQK YRGVRNGIFW GTWPGVSEAH PGGYKSSFKE AKMMIRPKHF
121 KP*
```

A.

B.

```
  1 MGHHHHHHHH HHSSGHIDDD DKMDAIKKKM QAMKLEKDNA MDRADTLEQQ NKEANNRAEK
 61 SEEEVFGLQK KLQQLENDLD SVQEALLKAN QHLEEKDKAL SNAEGEVAAL NRRIQLLEED
121 LERSEERLNT ATTKLAEASQ AADESERMRK VLENRSLSDE ERMDALENQL KEARFLAEEA
181 DRKYDEVARK LAMVEADLER AEERAETGES KIVELEEELR VVGNNLKSLE VSEEKANQRE
241 EAYKEQIKTL TNKLKAAEAR AEFAERSVQK LQKEVDRLED ELVNEKEKYK SITDELDQTF
301 SELSGYRADA APGDALRFNK HYNHDLKFFT TPDKDNDRYP SGNCGLYYSS GWWFDACLSA
361 NLNGKYYHQK YRGVRNGIFW GTWPGVSEAH PGGYKSSFKE AKMMIRPKHF KP*
```

Figure 4

Region 1                                                    Region 2

10         20         30         40         50         60         70         80         90        100        110        120        130        140
T   MDAIKKKMQAMKLEKDNAMDRADTLEQQNKEANNRAEKSEEEVFGLQKKLQQLENDLDSVQEALLKANQHLEEKDKALSNAEGEVAALNRRIQLLEEDLERSEERLNTATTKLAEASQAADESERMRKVLENRSLSDEERMD
P1  MDAIKKKMQAMKLEKDNAMDRADTLEQQNKEANNRAEKSEEEVFGLQKKLQQLENDLDSVQEALLKANQHLEEKDKAL
P2                                                                              HLEEKDKALSNAEGEVAALNRRIQLLEEDLERSEERLNTATTKLAEASQAADE SERMRKVLE
P3                                                                                                                          DESERMRKVLENRSLSDEERMD
P4
P5

Region 3                     Region 4                                            Region 5

150        160        170        180        190        200        210        220        230        240        250        260        270        280
T   ALENQLKEARFLAEEADRKYDEVARKLAMVEADLERAEERAETGESKIVELEELRVGNNLKSLEVSEEKANQREEAYKEQIKTLTNKLKAEARAEFAERSVQKLQKEVDRLEDELVNEKEKYKSITDELDQTFSELSGY
P1
P2
P3  ALENQLKEARFLAEEADRKYDEVARKLAMVEADLERAEE
P4                                       EADLERAEERAETGESKIVELEELRVGNNLKSLEVSEEKANQREEAYKEQIKTLTNKLKAAE
P5                                                                                                     KTLTNKLKAAEARAEFAERSVQKLQKEVDRLEDELVNEKEKYKSITDELDQTFSELSGY

Figure 7

A.

B.

```
  1 MGHHHHHHHH HHSSGHIDDD DKMDAIKKKM QAMKLEKDNA MDRADTLEQQ NKEANNRAEK
 61 SEEEVFGLQK KLQQLENDLD SVQEALLKAN QHLEEKDKAL RADAAPGDAL RFNKHYNHDL
121 KFFTTPDKDN DRYPSGNCGL YYSSGWWFDA CLSANLNGKY YHQKYRGVRN GIFWGTWPGV
181 SEAHPGGYKS SFKEAKMMIR PKHFKP*
```

C.

```
  1 MGHHHHHHHH HHSSGHIDDD DKKTLTNKLK AAEARAEFAE RSVQKLQKEV DRLEDELVNE
 61 KEKYKSITDE LDQTFSELSG YRADAAPGDA LRFNKHYNHD LKFFTTPDKD NDRYPSGNCG
121 LYYSSGWWFD ACLSANLNGK YYHQKYRGVR NGIFWGTWPG VSEAHPGGYK SSFKEAKMMI
181 RPKHFKP*
```

Figure 8

```
  1 MGHHHHHHHH HHSSGHIDDD DKGDALRFSR HYNHDLRFFT TPDRDNDRYP SGNCGLYYSS
 61 GWWFDSCLSA NLNGKYYHQK YKGVRNGIFW GTWPGINQAQ PGGYKSSFKQ AKMMIRPKNF
121 KP*
```

Figure 14

A.

B.

```
  1 MGHHHHHHHH HHSSGHIDDD DKMDAIKKKM QAMKLEKDNA MDRADTLEQQ NKEANNRAEK
 61 SEEEVFGLQK KLQQLENDLD SVQEALLKAN QHLEEKDKAL SNAEGEVAAL NRRIQLLEED
121 LERSEERLNT ATTKLAEASQ AADESERMRK VLENRSLSDE ERMDALENQL KEARFLAEEA
181 DRKYDEVARK LAMVEADLER AEERAETGES KIVELEEELR VVGNNLKSLE VSEEKANQRE
241 EAYKEQIKTL TNKLKAAEAR AEFAERSVQK LQKEVDRLED ELVNEKEKYK SITDELDQTF
301 SELSGYRADA APGDALRFSR HYNHDLRFFT TPDRDNDRYP SGNCGLYYSS GWWFDSCLSA
361 NLNGKYYHQK YKGVRNGIFW GTWPGINQAQ PGGYKSSFKQ AKMMIRPKNF KP*
```

Figure 16

Clinical and laboratory features of shrimp allergic individuals.

| Donor | Age | Sex | Dominating symptoms | Total IgE [kU/l] | sIgE Shrimp [kU$_A$/l] | sIgE rPen a 1 [kU$_A$/l] | SPT Shrimp [mm] | SPT Pan b 1 [mm] | Positive SPT to other invertebrates |
|---|---|---|---|---|---|---|---|---|---|
| A | 37 | M | Urticaria, dyspnoea | 242 | 56.3 | 38.9 | 9.5 | 6.2 | n.f. |
| B | 27 | M | Anaphylaxis | 328 | 35.7 | 39.9 | 5.0 | 8.7 | HDM |
| C | 49 | M | Urticaria | 71 | 5.52 | 4.02 | 6.4 | 6.8 | anisakis, artemia, HDM |
| D | 37 | F | Anaphylaxis | 780 | 6.26 | 5.07 | 7.0 | 7.1 | n.f. |
| E | 38 | F | Unknown | 51 | <0.35 | <0.35 | 4.0 | 7.0 | n.f. |
| F | 33 | M | Anaphylaxis | 124 | 24.5 | 18.10 | 13.3 | 10.4 | Anisakis, HDM | sIgE: Specific IgE
SPT: Skin prick test, mean duplicate wheal diameter (mm)
HDM: House dust mite
n.f.: None found

Figure 21

SEQUENCE LISTING

```
<160> NUMBER OF SEQ ID NOS: 52

<210> SEQ ID NO 1
<211> LENGTH: 122
<212> TYPE: PRT
<213> ORGANISM: Artificial Sequence
```

-continued

```
<220> FEATURE:
<223> OTHER INFORMATION: Human FGL2-C terminal peptide w His-Tag

<400> SEQUENCE: 1

Met Gly His His His His His His His His Ser Ser Gly His
1               5                   10                  15

Ile Asp Asp Asp Lys Gly Asp Ala Leu Arg Phe Asn Lys His Tyr
            20                  25                  30

Asn His Asp Leu Lys Phe Phe Thr Thr Pro Asp Lys Asp Asn Asp Arg
            35                  40                  45

Tyr Pro Ser Gly Asn Cys Gly Leu Tyr Tyr Ser Ser Gly Trp Trp Phe
        50                  55                  60

Asp Ala Cys Leu Ser Ala Asn Leu Asn Gly Lys Tyr Tyr His Gln Lys
65                  70                  75                  80

Tyr Arg Gly Val Arg Asn Gly Ile Phe Trp Gly Thr Trp Pro Gly Val
                85                  90                  95

Ser Glu Ala His Pro Gly Gly Tyr Lys Ser Ser Phe Lys Glu Ala Lys
            100                 105                 110

Met Met Ile Arg Pro Lys His Phe Lys Pro
            115                 120

<210> SEQ ID NO 2
<211> LENGTH: 412
<212> TYPE: PRT
<213> ORGANISM: Artificial Sequence
<220> FEATURE:
<223> OTHER INFORMATION: Histag-Tropomyosin-linker-CP, human protein

<400> SEQUENCE: 2

Met Gly His His His His His His His His Ser Ser Gly His
1               5                   10                  15

Ile Asp Asp Asp Lys Met Asp Ala Ile Lys Lys Lys Met Gln Ala
            20                  25                  30

Met Lys Leu Glu Lys Asp Asn Ala Met Asp Arg Ala Asp Thr Leu Glu
            35                  40                  45

Gln Gln Asn Lys Glu Ala Asn Asn Arg Ala Glu Lys Ser Glu Glu Glu
        50                  55                  60

Val Phe Gly Leu Gln Lys Lys Leu Gln Gln Leu Glu Asn Asp Leu Asp
65                  70                  75                  80

Ser Val Gln Glu Ala Leu Leu Lys Ala Asn Gln His Leu Glu Glu Lys
                85                  90                  95

Asp Lys Ala Leu Ser Asn Ala Glu Gly Glu Val Ala Ala Leu Asn Arg
            100                 105                 110

Arg Ile Gln Leu Leu Glu Glu Asp Leu Glu Arg Ser Glu Glu Arg Leu
            115                 120                 125

Asn Thr Ala Thr Thr Lys Leu Ala Glu Ala Ser Gln Ala Ala Asp Glu
            130                 135                 140

Ser Glu Arg Met Arg Lys Val Leu Glu Asn Arg Ser Leu Ser Asp Glu
145                 150                 155                 160

Glu Arg Met Asp Ala Leu Glu Asn Gln Leu Lys Glu Ala Arg Phe Leu
                165                 170                 175

Ala Glu Glu Ala Asp Arg Lys Tyr Asp Glu Val Ala Arg Lys Leu Ala
            180                 185                 190

Met Val Glu Ala Asp Leu Glu Arg Ala Glu Glu Arg Ala Glu Thr Gly
            195                 200                 205

Glu Ser Lys Ile Val Glu Leu Glu Glu Glu Leu Arg Val Val Gly Asn
```

```
                210                 215                 220
Asn Leu Lys Ser Leu Glu Val Ser Glu Glu Lys Ala Asn Gln Arg Glu
225                 230                 235                 240

Glu Ala Tyr Lys Glu Gln Ile Lys Thr Leu Thr Asn Lys Leu Lys Ala
                245                 250                 255

Ala Glu Ala Arg Ala Glu Phe Ala Glu Arg Ser Val Gln Lys Leu Gln
                260                 265                 270

Lys Glu Val Asp Arg Leu Glu Asp Glu Leu Val Asn Glu Lys Glu Lys
                275                 280                 285

Tyr Lys Ser Ile Thr Asp Glu Leu Asp Gln Thr Phe Ser Glu Leu Ser
                290                 295                 300

Gly Tyr Arg Ala Asp Ala Ala Pro Gly Asp Ala Leu Arg Phe Asn Lys
305                 310                 315                 320

His Tyr Asn His Asp Leu Lys Phe Phe Thr Thr Pro Asp Lys Asp Asn
                325                 330                 335

Asp Arg Tyr Pro Ser Gly Asn Cys Gly Leu Tyr Tyr Ser Ser Gly Trp
                340                 345                 350

Trp Phe Asp Ala Cys Leu Ser Ala Asn Leu Asn Gly Lys Tyr Tyr His
                355                 360                 365

Gln Lys Tyr Arg Gly Val Arg Asn Gly Ile Phe Trp Gly Thr Trp Pro
                370                 375                 380

Gly Val Ser Glu Ala His Pro Gly Gly Tyr Lys Ser Ser Phe Lys Glu
385                 390                 395                 400

Ala Lys Met Met Ile Arg Pro Lys His Phe Lys Pro
                405                 410

<210> SEQ ID NO 3
<211> LENGTH: 306
<212> TYPE: PRT
<213> ORGANISM: Artificial Sequence
<220> FEATURE:
<223> OTHER INFORMATION: recombinant Pan b 1 shrimp tropomyosin - Histag

<400> SEQUENCE: 3

Met Gly His His His His His His His His Ser Ser Gly His
1               5                   10                  15

Ile Asp Asp Asp Asp Lys Met Asp Ala Ile Lys Lys Lys Met Gln Ala
                20                  25                  30

Met Lys Leu Glu Lys Asp Asn Ala Met Asp Arg Ala Asp Thr Leu Glu
                35                  40                  45

Gln Gln Asn Lys Glu Ala Asn Asn Arg Ala Glu Lys Ser Glu Glu Glu
50                  55                  60

Val Phe Gly Leu Gln Lys Lys Leu Gln Gln Leu Glu Asn Asp Leu Asp
65                  70                  75                  80

Ser Val Gln Glu Ala Leu Leu Lys Ala Asn Gln His Leu Glu Glu Lys
                85                  90                  95

Asp Lys Ala Leu Ser Asn Ala Glu Gly Glu Val Ala Ala Leu Asn Arg
                100                 105                 110

Arg Ile Gln Leu Leu Glu Glu Asp Leu Glu Arg Ser Glu Glu Arg Leu
                115                 120                 125

Asn Thr Ala Thr Thr Lys Leu Ala Glu Ala Ser Gln Ala Ala Asp Glu
                130                 135                 140

Ser Glu Arg Met Arg Lys Val Leu Glu Asn Arg Ser Leu Ser Asp Glu
145                 150                 155                 160

Glu Arg Met Asp Ala Leu Glu Asn Gln Leu Lys Glu Ala Arg Phe Leu
```

```
                165                 170                 175
Ala Glu Glu Ala Asp Arg Lys Tyr Asp Glu Val Ala Arg Lys Leu Ala
            180                 185                 190

Met Val Glu Ala Asp Leu Glu Arg Ala Glu Arg Ala Glu Thr Gly
        195                 200                 205

Glu Ser Lys Ile Val Glu Leu Glu Glu Leu Arg Val Val Gly Asn
    210                 215                 220

Asn Leu Lys Ser Leu Glu Val Ser Glu Glu Lys Ala Asn Gln Arg Glu
225                 230                 235                 240

Glu Ala Tyr Lys Glu Gln Ile Lys Thr Leu Thr Asn Lys Leu Lys Ala
                245                 250                 255

Ala Glu Ala Arg Ala Glu Phe Ala Glu Arg Ser Val Gln Lys Leu Gln
            260                 265                 270

Lys Glu Val Asp Arg Leu Glu Asp Glu Leu Val Asn Glu Lys Glu Lys
        275                 280                 285

Tyr Lys Ser Ile Thr Asp Glu Leu Asp Gln Thr Phe Ser Glu Leu Ser
    290                 295                 300

Gly Tyr
305

<210> SEQ ID NO 4
<211> LENGTH: 78
<212> TYPE: PRT
<213> ORGANISM: Artificial Sequence
<220> FEATURE:
<223> OTHER INFORMATION: Pan b 1, peptide 1 shrimp pandalus borealis

<400> SEQUENCE: 4

Met Asp Ala Ile Lys Lys Lys Met Gln Ala Met Lys Leu Glu Lys Asp
1               5                   10                  15

Asn Ala Met Asp Arg Ala Asp Thr Leu Glu Gln Gln Asn Lys Glu Ala
            20                  25                  30

Asn Asn Arg Ala Glu Lys Ser Glu Glu Glu Val Phe Gly Leu Gln Lys
        35                  40                  45

Lys Leu Gln Gln Leu Glu Asn Asp Leu Asp Ser Val Gln Glu Ala Leu
    50                  55                  60

Leu Lys Ala Asn Gln His Leu Glu Glu Lys Asp Lys Ala Leu
65                  70                  75

<210> SEQ ID NO 5
<211> LENGTH: 62
<212> TYPE: PRT
<213> ORGANISM: Artificial Sequence
<220> FEATURE:
<223> OTHER INFORMATION: Pan b 1, peptide 2

<400> SEQUENCE: 5

His Leu Glu Glu Lys Asp Lys Ala Leu Ser Asn Ala Glu Gly Glu Val
1               5                   10                  15

Ala Ala Leu Asn Arg Arg Ile Gln Leu Leu Glu Glu Asp Leu Glu Arg
            20                  25                  30

Ser Glu Glu Arg Leu Asn Thr Ala Thr Thr Lys Leu Ala Glu Ala Ser
        35                  40                  45

Gln Ala Ala Asp Glu Ser Glu Arg Met Arg Lys Val Leu Glu
    50                  55                  60

<210> SEQ ID NO 6
<211> LENGTH: 61
```

```
<212> TYPE: PRT
<213> ORGANISM: Artificial Sequence
<220> FEATURE:
<223> OTHER INFORMATION: Pan b 1, peptide 3

<400> SEQUENCE: 6

Asp Glu Ser Glu Arg Met Arg Lys Val Leu Glu Asn Arg Ser Leu Ser
1               5                   10                  15

Asp Glu Glu Arg Met Asp Ala Leu Glu Asn Gln Leu Lys Glu Ala Arg
            20                  25                  30

Phe Leu Ala Glu Glu Ala Asp Arg Lys Tyr Asp Glu Val Ala Arg Lys
        35                  40                  45

Leu Ala Met Val Glu Ala Asp Leu Glu Arg Ala Glu Glu
        50                  55                  60

<210> SEQ ID NO 7
<211> LENGTH: 64
<212> TYPE: PRT
<213> ORGANISM: Artificial Sequence
<220> FEATURE:
<223> OTHER INFORMATION: Pan b 1, peptide no 4

<400> SEQUENCE: 7

Glu Ala Asp Leu Glu Arg Ala Glu Glu Arg Ala Glu Thr Gly Glu Ser
1               5                   10                  15

Lys Ile Val Glu Leu Glu Glu Glu Leu Arg Val Val Gly Asn Asn Leu
            20                  25                  30

Lys Ser Leu Glu Val Ser Glu Glu Lys Ala Asn Gln Arg Glu Glu Ala
        35                  40                  45

Tyr Lys Glu Gln Ile Lys Thr Leu Thr Asn Lys Leu Lys Ala Ala Glu
        50                  55                  60

<210> SEQ ID NO 8
<211> LENGTH: 59
<212> TYPE: PRT
<213> ORGANISM: Artificial Sequence
<220> FEATURE:
<223> OTHER INFORMATION: Pan b 1, peptide no 5

<400> SEQUENCE: 8

Lys Thr Leu Thr Asn Lys Leu Lys Ala Ala Glu Ala Arg Ala Glu Phe
1               5                   10                  15

Ala Glu Arg Ser Val Gln Lys Leu Gln Lys Glu Val Asp Arg Leu Glu
            20                  25                  30

Asp Glu Leu Val Asn Glu Lys Glu Lys Tyr Lys Ser Ile Thr Asp Glu
        35                  40                  45

Leu Asp Gln Thr Phe Ser Glu Leu Ser Gly Tyr
        50                  55

<210> SEQ ID NO 9
<211> LENGTH: 22
<212> TYPE: PRT
<213> ORGANISM: Artificial Sequence
<220> FEATURE:
<223> OTHER INFORMATION: Histidine tag Protein

<400> SEQUENCE: 9

Met Gly His His His His His His His His His Ser Ser Gly His
1               5                   10                  15

Ile Asp Asp Asp Asp Lys
            20
```

<210> SEQ ID NO 10
<211> LENGTH: 206
<212> TYPE: PRT
<213> ORGANISM: Artificial Sequence
<220> FEATURE:
<223> OTHER INFORMATION: FP with tropomyosine peptide 1 protein

<400> SEQUENCE: 10

```
Met Gly His His His His His His His His Ser Ser Gly His
1               5                   10                  15

Ile Asp Asp Asp Lys Met Asp Ala Ile Lys Lys Met Gln Ala
            20                  25                  30

Met Lys Leu Glu Lys Asp Asn Ala Met Asp Arg Ala Asp Thr Leu Glu
        35                  40                  45

Gln Gln Asn Lys Glu Ala Asn Asn Arg Ala Glu Lys Ser Glu Glu
    50                  55                  60

Val Phe Gly Leu Gln Lys Lys Leu Gln Gln Leu Glu Asn Asp Leu Asp
65              70                  75                  80

Ser Val Gln Glu Ala Leu Leu Lys Ala Asn Gln His Leu Glu Glu Lys
            85                  90                  95

Asp Lys Ala Leu Arg Ala Asp Ala Ala Pro Gly Asp Ala Leu Arg Phe
            100                 105                 110

Asn Lys His Tyr Asn His Asp Leu Lys Phe Phe Thr Thr Pro Asp Lys
            115                 120                 125

Asp Asn Asp Arg Tyr Pro Ser Gly Asn Cys Gly Leu Tyr Tyr Ser Ser
130                 135                 140

Gly Trp Trp Phe Asp Ala Cys Leu Ser Ala Asn Leu Asn Gly Lys Tyr
145                 150                 155                 160

Tyr His Gln Lys Tyr Arg Gly Val Arg Asn Gly Ile Phe Trp Gly Thr
                165                 170                 175

Trp Pro Gly Val Ser Glu Ala His Pro Gly Gly Tyr Lys Ser Ser Phe
            180                 185                 190

Lys Glu Ala Lys Met Met Ile Arg Pro Lys His Phe Lys Pro
        195                 200                 205
```

<210> SEQ ID NO 11
<211> LENGTH: 187
<212> TYPE: PRT
<213> ORGANISM: Artificial Sequence
<220> FEATURE:
<223> OTHER INFORMATION: FP with tropomyosin peptide no 5 protein

<400> SEQUENCE: 11

```
Met Gly His His His His His His His His Ser Ser Gly His
1               5                   10                  15

Ile Asp Asp Asp Lys Lys Thr Leu Thr Asn Lys Leu Lys Ala Ala
            20                  25                  30

Glu Ala Arg Ala Glu Phe Ala Glu Arg Ser Val Gln Lys Leu Gln Lys
        35                  40                  45

Glu Val Asp Arg Leu Glu Asp Glu Leu Val Asn Glu Lys Glu Lys Tyr
    50                  55                  60

Lys Ser Ile Thr Asp Glu Leu Asp Gln Thr Phe Ser Glu Leu Ser Gly
65              70                  75                  80

Tyr Arg Ala Asp Ala Ala Pro Gly Asp Ala Leu Arg Phe Asn Lys His
                85                  90                  95

Tyr Asn His Asp Leu Lys Phe Phe Thr Thr Pro Asp Lys Asp Asn Asp
            100                 105                 110
```

Arg Tyr Pro Ser Gly Asn Cys Gly Leu Tyr Tyr Ser Gly Trp Trp
            115                 120                 125

Phe Asp Ala Cys Leu Ser Ala Asn Leu Asn Gly Lys Tyr Tyr His Gln
    130                 135                 140

Lys Tyr Arg Gly Val Arg Asn Gly Ile Phe Trp Gly Thr Trp Pro Gly
145                 150                 155                 160

Val Ser Glu Ala His Pro Gly Gly Tyr Lys Ser Ser Phe Lys Glu Ala
                165                 170                 175

Lys Met Met Ile Arg Pro Lys His Phe Lys Pro
                180                 185

<210> SEQ ID NO 12
<211> LENGTH: 6
<212> TYPE: PRT
<213> ORGANISM: Artificial Sequence
<220> FEATURE:
<223> OTHER INFORMATION: Linker

<400> SEQUENCE: 12

Arg Ala Asp Ala Ala Pro
1               5

<210> SEQ ID NO 13
<211> LENGTH: 122
<212> TYPE: PRT
<213> ORGANISM: Artificial Sequence
<220> FEATURE:
<223> OTHER INFORMATION: Mouse FGL-C terminal peptide (CP) - histag

<400> SEQUENCE: 13

Met Gly His His His His His His His His Ser Ser Gly His
1               5                   10                  15

Ile Asp Asp Asp Asp Lys Gly Asp Ala Leu Arg Phe Ser Arg His Tyr
                20                  25                  30

Asn His Asp Leu Arg Phe Phe Thr Thr Pro Asp Arg Asn Asp Arg
            35                  40                  45

Tyr Pro Ser Gly Asn Cys Gly Leu Tyr Tyr Ser Ser Gly Trp Trp Phe
    50                  55                  60

Asp Ser Cys Leu Ser Ala Asn Leu Asn Gly Lys Tyr Tyr His Gln Lys
65                  70                  75                  80

Tyr Lys Gly Val Arg Asn Gly Ile Phe Trp Gly Thr Trp Pro Gly Ile
                85                  90                  95

Asn Gln Ala Gln Pro Gly Gly Tyr Lys Ser Ser Phe Lys Gln Ala Lys
            100                 105                 110

Met Met Ile Arg Pro Lys Asn Phe Lys Pro
        115                 120

<210> SEQ ID NO 14
<211> LENGTH: 412
<212> TYPE: PRT
<213> ORGANISM: Artificial Sequence
<220> FEATURE:
<223> OTHER INFORMATION: Fusion proteins with mouse FGL2 peptide,
      protein sequence

<400> SEQUENCE: 14

Met Gly His His His His His His His His Ser Ser Gly His
1               5                   10                  15

Ile Asp Asp Asp Asp Lys Met Asp Ala Ile Lys Lys Met Gln Ala
                20                  25                  30

```
Met Lys Leu Glu Lys Asp Asn Ala Met Asp Arg Ala Asp Thr Leu Glu
            35                  40                  45
Gln Gln Asn Lys Glu Ala Asn Asn Arg Ala Glu Lys Ser Glu Glu Glu
 50                  55                  60
Val Phe Gly Leu Gln Lys Lys Leu Gln Gln Leu Glu Asn Asp Leu Asp
 65                  70                  75                  80
Ser Val Gln Glu Ala Leu Leu Lys Ala Asn Gln His Leu Glu Glu Lys
                85                  90                  95
Asp Lys Ala Leu Ser Asn Ala Glu Gly Glu Val Ala Ala Leu Asn Arg
            100                 105                 110
Arg Ile Gln Leu Leu Glu Glu Asp Leu Glu Arg Ser Glu Glu Arg Leu
            115                 120                 125
Asn Thr Ala Thr Thr Lys Leu Ala Glu Ala Ser Gln Ala Ala Asp Glu
 130                 135                 140
Ser Glu Arg Met Arg Lys Val Leu Glu Asn Arg Ser Leu Ser Asp Glu
145                 150                 155                 160
Glu Arg Met Asp Ala Leu Glu Asn Gln Leu Lys Glu Ala Arg Phe Leu
                165                 170                 175
Ala Glu Glu Ala Asp Arg Lys Tyr Asp Glu Val Ala Arg Lys Leu Ala
            180                 185                 190
Met Val Glu Ala Asp Leu Glu Arg Ala Glu Glu Arg Ala Glu Thr Gly
            195                 200                 205
Glu Ser Lys Ile Val Glu Leu Glu Glu Glu Leu Arg Val Val Gly Asn
            210                 215                 220
Asn Leu Lys Ser Leu Glu Val Ser Glu Glu Lys Ala Asn Gln Arg Glu
225                 230                 235                 240
Glu Ala Tyr Lys Glu Gln Ile Lys Thr Leu Thr Asn Lys Leu Lys Ala
                245                 250                 255
Ala Glu Ala Arg Ala Glu Phe Ala Glu Arg Ser Val Gln Lys Leu Gln
            260                 265                 270
Lys Glu Val Asp Arg Leu Glu Asp Glu Leu Val Asn Glu Lys Glu Lys
            275                 280                 285
Tyr Lys Ser Ile Thr Asp Glu Leu Asp Gln Thr Phe Ser Glu Leu Ser
290                 295                 300
Gly Tyr Arg Ala Asp Ala Ala Pro Gly Asp Ala Leu Arg Phe Ser Arg
305                 310                 315                 320
His Tyr Asn His Asp Leu Arg Phe Phe Thr Thr Pro Asp Arg Asp Asn
                325                 330                 335
Asp Arg Tyr Pro Ser Gly Asn Cys Gly Leu Tyr Tyr Ser Ser Gly Trp
            340                 345                 350
Trp Phe Asp Ser Cys Leu Ser Ala Asn Leu Asn Gly Lys Tyr Tyr His
            355                 360                 365
Gln Lys Tyr Lys Gly Val Arg Asn Gly Ile Phe Trp Gly Thr Trp Pro
            370                 375                 380
Gly Ile Asn Gln Ala Gln Pro Gly Gly Tyr Lys Ser Ser Phe Lys Gln
385                 390                 395                 400
Ala Lys Met Met Ile Arg Pro Lys Asn Phe Lys Pro
                405                 410

<210> SEQ ID NO 15
<211> LENGTH: 284
<212> TYPE: PRT
<213> ORGANISM: Artificial Sequence
<220> FEATURE:
```

<223> OTHER INFORMATION: Pan b 1 shrimp tropomyosin pandalus borealis

<400> SEQUENCE: 15

```
Met Asp Ala Ile Lys Lys Met Gln Ala Met Lys Leu Glu Lys Asp
 1               5                  10                  15
Asn Ala Met Asp Arg Ala Asp Thr Leu Glu Gln Gln Asn Lys Glu Ala
            20                  25                  30
Asn Asn Arg Ala Glu Lys Ser Glu Glu Val Phe Gly Leu Gln Lys
        35                  40                  45
Lys Leu Gln Gln Leu Glu Asn Asp Leu Asp Ser Val Gln Glu Ala Leu
50                  55                  60
Leu Lys Ala Asn Gln His Leu Glu Glu Lys Asp Lys Ala Leu Ser Asn
65                  70                  75                  80
Ala Glu Gly Glu Val Ala Ala Leu Asn Arg Arg Ile Gln Leu Leu Glu
                85                  90                  95
Glu Asp Leu Glu Arg Ser Glu Glu Arg Leu Asn Thr Ala Thr Thr Lys
            100                 105                 110
Leu Ala Glu Ala Ser Gln Ala Ala Asp Glu Ser Glu Arg Met Arg Lys
        115                 120                 125
Val Leu Glu Asn Arg Ser Leu Ser Asp Glu Glu Arg Met Asp Ala Leu
130                 135                 140
Glu Asn Gln Leu Lys Glu Ala Arg Phe Leu Ala Glu Glu Ala Asp Arg
145                 150                 155                 160
Lys Tyr Asp Glu Val Ala Arg Lys Leu Ala Met Val Glu Ala Asp Leu
                165                 170                 175
Glu Arg Ala Glu Arg Ala Glu Thr Gly Glu Ser Lys Ile Val Glu
            180                 185                 190
Leu Glu Glu Glu Leu Arg Val Val Gly Asn Asn Leu Lys Ser Leu Glu
        195                 200                 205
Val Ser Glu Glu Lys Ala Asn Gln Arg Glu Glu Ala Tyr Lys Glu Gln
210                 215                 220
Ile Lys Thr Leu Thr Asn Lys Leu Lys Ala Ala Glu Ala Arg Ala Glu
225                 230                 235                 240
Phe Ala Glu Arg Ser Val Gln Lys Leu Gln Lys Glu Val Asp Arg Leu
                245                 250                 255
Glu Asp Glu Leu Val Asn Glu Lys Glu Lys Tyr Lys Ser Ile Thr Asp
            260                 265                 270
Glu Leu Asp Gln Thr Phe Ser Glu Leu Ser Gly Tyr
        275                 280
```

<210> SEQ ID NO 16
<211> LENGTH: 36
<212> TYPE: DNA
<213> ORGANISM: Artificial Sequence
<220> FEATURE:
<223> OTHER INFORMATION: recombinant shrimp tropomyosin fwd primer

<400> SEQUENCE: 16
gacgacgacg acaagatgga cgccatcaag aagaag                      36

<210> SEQ ID NO 17
<211> LENGTH: 38
<212> TYPE: DNA
<213> ORGANISM: Artificial Sequence
<220> FEATURE:
<223> OTHER INFORMATION: recombinant shrimp tropomyosin rew primer

<400> SEQUENCE: 17

```
gctttgttag cagccttagt agccagacag ttcgctga                           38
```

<210> SEQ ID NO 18
<211> LENGTH: 39
<212> TYPE: DNA
<213> ORGANISM: Artificial Sequence
<220> FEATURE:
<223> OTHER INFORMATION: P1 fwd primer

<400> SEQUENCE: 18

```
gacgacgacg acaagatgga cgccatcaag aagaagatg                          39
```

<210> SEQ ID NO 19
<211> LENGTH: 42
<212> TYPE: DNA
<213> ORGANISM: Artificial Sequence
<220> FEATURE:
<223> OTHER INFORMATION: P1 rew primer

<400> SEQUENCE: 19

```
gctttgttag cagccttaga gagccttgtc cttctcctca ag                      42
```

<210> SEQ ID NO 20
<211> LENGTH: 36
<212> TYPE: DNA
<213> ORGANISM: Artificial Sequence
<220> FEATURE:
<223> OTHER INFORMATION: P2 fwd primer

<400> SEQUENCE: 20

```
gacgacgacg acaaggaagc tctgctgaag gctaac                             36
```

<210> SEQ ID NO 21
<211> LENGTH: 38
<212> TYPE: DNA
<213> ORGANISM: Artificial Sequence
<220> FEATURE:
<223> OTHER INFORMATION: P2 rew primer

<400> SEQUENCE: 21

```
gctttgttag cagccttact cgagcacctt gcgcatac                           38
```

<210> SEQ ID NO 22
<211> LENGTH: 33
<212> TYPE: DNA
<213> ORGANISM: Artificial Sequence
<220> FEATURE:
<223> OTHER INFORMATION: P3 fwd primer

<400> SEQUENCE: 22

```
gacgacgacg acaaggacga gtccgagcgt atg                                33
```

<210> SEQ ID NO 23
<211> LENGTH: 36
<212> TYPE: DNA
<213> ORGANISM: Artificial Sequence
<220> FEATURE:
<223> OTHER INFORMATION: P3 rew primer

<400> SEQUENCE: 23

```
gctttgttag cagccttact cctctgctcg ctcaag                             36
```

<210> SEQ ID NO 24
<211> LENGTH: 39
<212> TYPE: DNA

```
<213> ORGANISM: Artificial Sequence
<220> FEATURE:
<223> OTHER INFORMATION: P4 fwd primer

<400> SEQUENCE: 24
gacgacgacg acaaggaagc tgatcttgag cgagcagag                              39

<210> SEQ ID NO 25
<211> LENGTH: 38
<212> TYPE: DNA
<213> ORGANISM: Artificial Sequence
<220> FEATURE:
<223> OTHER INFORMATION: P4 rew primer

<400> SEQUENCE: 25
gctttgttag cagccttact cagccgcctt cagcttgt                               38

<210> SEQ ID NO 26
<211> LENGTH: 39
<212> TYPE: DNA
<213> ORGANISM: Artificial Sequence
<220> FEATURE:
<223> OTHER INFORMATION: P5 fwd primer

<400> SEQUENCE: 26
gacgacgacg acaagaagac tctcaccaac aagctgaag                              39

<210> SEQ ID NO 27
<211> LENGTH: 38
<212> TYPE: DNA
<213> ORGANISM: Artificial Sequence
<220> FEATURE:
<223> OTHER INFORMATION: P5 rew primer

<400> SEQUENCE: 27
gctttgttag cagccttagt agccagacag ttcgctga                               38

<210> SEQ ID NO 28
<211> LENGTH: 30
<212> TYPE: DNA
<213> ORGANISM: Artificial Sequence
<220> FEATURE:
<223> OTHER INFORMATION: Human FGL2 CP fwd primer

<400> SEQUENCE: 28
gacgacgacg acaagggaga tgcattacgt                                        30

<210> SEQ ID NO 29
<211> LENGTH: 45
<212> TYPE: DNA
<213> ORGANISM: Artificial Sequence
<220> FEATURE:
<223> OTHER INFORMATION: Human FGL2 CP rew prim

<400> SEQUENCE: 29
gctttgttag cagcccagag tgatttatgg cttaaagtgc ttggg                       45

<210> SEQ ID NO 30
<211> LENGTH: 30
<212> TYPE: DNA
<213> ORGANISM: Artificial Sequence
<220> FEATURE:
<223> OTHER INFORMATION: Mouse FGL2 mCP fwd primer

<400> SEQUENCE: 30
gacgacgacg acaagggga tgccttgcgt                                         30
```

<210> SEQ ID NO 31
<211> LENGTH: 45
<212> TYPE: DNA
<213> ORGANISM: Artificial Sequence
<220> FEATURE:
<223> OTHER INFORMATION: Mouse FGL2 mCP rew peptide

<400> SEQUENCE: 31
gctttgttag cagcccagag tgatttatgg cttgaaattc ttggg            45

<210> SEQ ID NO 32
<211> LENGTH: 36
<212> TYPE: DNA
<213> ORGANISM: Artificial Sequence
<220> FEATURE:
<223> OTHER INFORMATION: FP tropomyosin fwd primer

<400> SEQUENCE: 32
gacgacgacg acaagatgga cgccatcaag aagaag                      36

<210> SEQ ID NO 33
<211> LENGTH: 38
<212> TYPE: DNA
<213> ORGANISM: Artificial Sequence
<220> FEATURE:
<223> OTHER INFORMATION: FP tropomyosin rew primer

<400> SEQUENCE: 33
tggtgcagca tcagcccggt agccagacag ttcgctga                    38

<210> SEQ ID NO 34
<211> LENGTH: 33
<212> TYPE: DNA
<213> ORGANISM: Artificial Sequence
<220> FEATURE:
<223> OTHER INFORMATION: FP FGL2-peptide_fp fwd prim

<400> SEQUENCE: 34
cgggctgatg ctgcaccagg agatgcatta cgt                         33

<210> SEQ ID NO 35
<211> LENGTH: 45
<212> TYPE: DNA
<213> ORGANISM: Artificial Sequence
<220> FEATURE:
<223> OTHER INFORMATION: Fusion protein FGL2 pep 2

<400> SEQUENCE: 35
gctttgttag cagcccagag tgatttatgg cttaaagtgc ttggg            45

<210> SEQ ID NO 36
<211> LENGTH: 39
<212> TYPE: DNA
<213> ORGANISM: Artificial Sequence
<220> FEATURE:
<223> OTHER INFORMATION: Fusion protein with tropomyosin P1 and human
     FGL2peptide, peptide 1 rew prim

<400> SEQUENCE: 36
tggtgcagca tcagcccgga gagccttgtc cttctcctc                   39

<210> SEQ ID NO 37
<211> LENGTH: 39
<212> TYPE: DNA
<213> ORGANISM: Artificial Sequence
<220> FEATURE:
<223> OTHER INFORMATION: Fusion protein with tropomyosin P5 and human
      FGL2peptide fwd primer

<400> SEQUENCE: 37
gacgacgacg acaagaagac tctcaccaac aagctgaag                39

<210> SEQ ID NO 38
<211> LENGTH: 38
<212> TYPE: DNA
<213> ORGANISM: Artificial Sequence
<220> FEATURE:
<223> OTHER INFORMATION: Fusion protein with tropomyosin P5 and human
      FGL2peptide, rew primer

<400> SEQUENCE: 38
gctttgttag cagccttagt agccagacag ttcgctga                 38

<210> SEQ ID NO 39
<211> LENGTH: 36
<212> TYPE: DNA
<213> ORGANISM: Artificial Sequence
<220> FEATURE:
<223> OTHER INFORMATION: Fusion protein with whole tropomyosin and mouse
      FGL2peptide, fwd primer

<400> SEQUENCE: 39
gacgacgacg acaagatgga cgccatcaag aagaag                   36

<210> SEQ ID NO 40
<211> LENGTH: 38
<212> TYPE: DNA
<213> ORGANISM: Artificial Sequence
<220> FEATURE:
<223> OTHER INFORMATION: Fusion protein with whole tropomyosin and mouse
      FGL2peptide, rew primer

<400> SEQUENCE: 40
tggtgcagca tcagcccggt agccagacag ttcgctga                 38

<210> SEQ ID NO 41
<211> LENGTH: 33
<212> TYPE: DNA
<213> ORGANISM: Artificial Sequence
<220> FEATURE:
<223> OTHER INFORMATION: Mouse FGL2 peptide for fusion protein fwd
      primer

<400> SEQUENCE: 41
cgggctgatg ctgcaccagg ggatgccttg cgt                      33

<210> SEQ ID NO 42
<211> LENGTH: 45
<212> TYPE: DNA
<213> ORGANISM: Artificial Sequence
<220> FEATURE:
<223> OTHER INFORMATION: Mouse FGL2 peptide for fusion protein rev
      primer

<400> SEQUENCE: 42
gctttgttag cagcccagag tgatttatgg cttgaaattc ttggg         45

<210> SEQ ID NO 43
<211> LENGTH: 993
<212> TYPE: DNA
<213> ORGANISM: Artificial Sequence
<220> FEATURE:

<223> OTHER INFORMATION: Shrimp allergens from pandalus borealis: Pan
b 1

<400> SEQUENCE: 43

| | | | | | |
|---|---|---|---|---|---|
| gttagaacct | cctcctaaaa | caccgccatc | atggacgcca | tcaagaagaa | gatgcaggct | 60 |
| atgaagctcg | agaaggacaa | cgccatggac | agggcggata | ctctcgagca | gcagaacaag | 120 |
| gaggccaaca | cagggctga | gaagtccgag | gaggaggttt | tcggccttca | gaagaagctg | 180 |
| cagcagcttg | agaacgacct | cgacagtgta | caggaagctc | tgctgaaggc | taaccaacac | 240 |
| cttgaggaga | aggacaaggc | tctctctaac | gctgagggtg | aggttgccgc | tcttaaccgt | 300 |
| cgcatccagc | ttctagagga | ggacctcgag | aggtctgagg | agcgactcaa | cactgccacc | 360 |
| accaagttgg | ccgaggcttc | ccaggcagcc | gacgagtccg | agcgtatgcg | caaggtgctc | 420 |
| gagaatcgtt | ccctctccga | cgaggagcgc | atggacgccc | tcgagaacca | actcaaggaa | 480 |
| gcccgattcc | tggctgaaga | agccgacagg | aaatacgacg | aggtcgcccg | taagctggcc | 540 |
| atggttgaag | ctgatcttga | gcgagcgag | gagcgcgccg | agaccggtga | atcaaagatc | 600 |
| gttgagcttg | aggaggagct | ccgcgtcgtt | ggcaacaacc | tgaagtctct | cgaagtgtcc | 660 |
| gaggagaagg | ccaaccagcg | tgaagaagcc | tacaaggaac | agattaagac | tctcaccaac | 720 |
| aagctgaagg | cggctgaggc | ccgcgctgag | ttcgctgaga | gatctgtgca | gaagctccag | 780 |
| aaggaggtcg | acaggctcga | agacgaactg | gttaacgaaa | aggagaagta | caagtcaatt | 840 |
| accgacgagc | tcgaccagac | tttcagcgaa | ctgtctggct | actaaacact | ctctgctcca | 900 |
| aaaacctcct | cttctgccac | ctctctatta | tgctattgcc | cctcagctgg | cctgtataac | 960 |
| cttactatca | tttaaacaaa | aaaaagctta | ttt | | | 993 |

<210> SEQ ID NO 44
<211> LENGTH: 1059
<212> TYPE: DNA
<213> ORGANISM: Artificial Sequence
<220> FEATURE:
<223> OTHER INFORMATION: Recombinant Pan b 1 (shrimp, pandalus borealis)

<400> SEQUENCE: 44

| | | | | | |
|---|---|---|---|---|---|
| atgggccatc | atcatcatca | tcatcatcat | catcacagca | gcggccatat | cgacgacgac | 60 |
| gacaaggtta | gaacctcctc | ctaaaacacc | gccatcatgg | acgccatcaa | gaagaagatg | 120 |
| caggctatga | agctcgagaa | ggacaacgcc | atggacaggg | cggatactct | cgagcagcag | 180 |
| aacaaggagg | ccaacaacag | ggctgagaag | tccgaggagg | aggttttcgg | ccttcagaag | 240 |
| aagctgcagc | agcttgagaa | cgacctcgac | agtgtacagg | aagctctgct | gaaggctaac | 300 |
| caacaccttg | aggagaagga | caaggctctc | tctaacgctg | agggtgaggt | tgccgctctt | 360 |
| aaccgtcgca | tccagcttct | agaggaggac | ctcgagaggt | ctgaggagcg | actcaacact | 420 |
| gccaccacca | agttggccga | ggcttcccag | gcagccgacg | agtccgagcg | tatgcgcaag | 480 |
| gtgctcgaga | atcgttccct | ctccgacgag | gagcgcatgg | acgccctcga | gaaccaactc | 540 |
| aaggaagccc | gattcctggc | tgaagaagcc | gacaggaaat | acgacgaggt | cgcccgtaag | 600 |
| ctggccatgg | ttgaagctga | tcttgagcga | gcagaggagc | gcgccgagac | cggtgaatca | 660 |
| aagatcgttg | agcttgagga | ggagctccgc | gtcgttggca | acaacctgaa | gtctctcgaa | 720 |
| gtgtccgagg | agaaggccaa | ccagcgtgaa | gaagcctaca | aggaacagat | taagactctc | 780 |
| accaacaagc | tgaaggcggc | tgaggcccgc | gctgagttcg | ctgagagatc | tgtgcagaag | 840 |
| ctccagaagg | aggtcgacag | gctcgaagac | gaactggtta | acgaaaagga | gaagtacaag | 900 |

```
tcaattaccg acgagctcga ccagactttc agcgaactgt ctggctacta aacactctct    960
gctccaaaaa cctcctcttc tgccacctct ctattatgct attgcccctc agctggcctg   1020 tataaccta ctatcattta acaaaaaaa agcttattt                            1059
```

<210> SEQ ID NO 45
<211> LENGTH: 66
<212> TYPE: DNA
<213> ORGANISM: Artificial Sequence
<220> FEATURE:
<223> OTHER INFORMATION: Histidin tag (artificial):

<400> SEQUENCE: 45

```
atgggccatc atcatcatca tcatcatcat catcacagca gcggccatat cgacgacgac     60
gacaag                                                                66
```

<210> SEQ ID NO 46
<211> LENGTH: 16
<212> TYPE: DNA
<213> ORGANISM: Artificial Sequence
<220> FEATURE:
<223> OTHER INFORMATION: Linker

<400> SEQUENCE: 46

```
cgggctgatg ctgcac                                                     16
```

<210> SEQ ID NO 47
<211> LENGTH: 369
<212> TYPE: DNA
<213> ORGANISM: Artificial Sequence
<220> FEATURE:
<223> OTHER INFORMATION: Human FGL2-C terminal peptide (CP), nt sequence

<400> SEQUENCE: 47

```
atgggccatc atcatcatca tcatcatcat catcacagca gcggccatat cgacgacgac     60 gacaaggag atgcattacg tttcaacaaa cattacaacc acgatctgaa gttttcacc     120 actccagata aagacaatga tcgatatcct tctgggaact gtgggctgta ctacagttca    180
ggctggtggt ttgatgcatg tctttctgca aacttaaatg caaatatta tcaccaaaaa    240 tacagaggtg tccgtaatgg gattttctgg ggtacctggc ctggtgtaag tgaggcacac    300
cctggtggct acaagtcctc cttcaaagag gctaagatga tgatcagacc caagcacttt    360
aagccataa                                                            369
```

<210> SEQ ID NO 48
<211> LENGTH: 369
<212> TYPE: DNA
<213> ORGANISM: Artificial Sequence
<220> FEATURE:
<223> OTHER INFORMATION: Mouse FGL2-C terminal peptide (CP), nt sequence

<400> SEQUENCE: 48

```
atgggccatc atcatcatca tcatcatcat catcacagca gcggccatat cgacgacgac     60
gacaaggggg atgccttgcg tttcagtcga cactacaacc atgacctgag gttttcaca    120 accccagaca gagacaacga tcggtacccc tctgggaact gtgggctcta ttacagctca    180
ggctggtggt ttgattcatg tctctctgcc aacttaaatg caaatatta ccaccagaaa    240 tacaaaggtg tccgtaatgg gattttctgg ggcacctggc tggtataaa ccaggcacag    300 ccaggtggct acaagtcctc cttcaaacag gccaagatga tgattaggcc caagaatttc    360
aagccataa                                                            369
```

<210> SEQ ID NO 49
<211> LENGTH: 1239
<212> TYPE: DNA
<213> ORGANISM: Artificial Sequence
<220> FEATURE:
<223> OTHER INFORMATION: Fusion proteins with human FGL2 peptide:
    Histag-Tropomyosin-linker-CP, nt sequence

<400> SEQUENCE: 49

| | | |
|---|---|---|
| atgggccatc atcatcatca tcatcatcat catcacagca gcggccatat cgacgacgac | 60 |
| gacaagatgg acgccatcaa gaagaagatg caggctatga agctcgagaa ggacaacgcc | 120 |
| atggacaggg cggatactct cgagcagcag aacaaggagg ccaacaacag ggctgagaag | 180 |
| tccgaggagg aggttttcgg ccttcagaag aagctgcagc agcttgagaa cgacctcgac | 240 |
| agtgtacagg aagctctgct gaaggctaac caacaccttg aggagaagga caaggctctc | 300 |
| tctaacgctg gggtgaggt tgccgctctt aaccgtcgca tccagcttct agaggaggac | 360 |
| ctcgagaggt ctgaggagcg actcaacact gccaccacca gttggccgga ggcttcccag | 420 |
| gcagccgacg agtccgagcg tatgcgcaag gtgctcgaga tcgttccct ctccgacgag | 480 |
| gagcgcatgg acgccctcga gaaccaactc aaggaagccc gattcctggc tgaagaagcc | 540 |
| gacaggaaat acgacgaggt cgcccgtaag ctggccatgg ttgaagctga tcttgagcga | 600 |
| gcagaggagc gcgccgagac cggtgaatca agatcgttg agcttgagga ggagctccgc | 660 |
| gtcgttggca caacctgaa gtctctcgaa gtgtccgagg agaaggccaa ccagcgtgaa | 720 |
| gaagcctaca ggaacagat taagactctc accaacaagc tgaaggcggc tgaggcccgc | 780 |
| gctgagttcg ctgagagatc tgtgcagaag ctccagaagg aggtcgacag gctcgaagac | 840 |
| gaactggtta cgaaaagga gaagtacaag tcaattaccg acgagctcga ccagactttc | 900 |
| agcgaactgt ctggctaccg ggctgatgct gcaccaggag atgcattacg tttcaacaaa | 960 |
| cattacaacc acgatctgaa gttttcacc actccagata agacaatga tcgatatcct | 1020 |
| tctgggaact gtgggctgta ctacagttca ggctggtggt tgatgcatg tctttctgca | 1080 |
| aacttaaatg gcaaatatta tcaccaaaaa tacagaggtg tccgtaatgg gattttctgg | 1140 |
| ggtacctggc ctggtgtaag tgaggcacac cctggtggct acaagtcctc cttcaaagag | 1200 |
| gctaagatga tgatcagacc caagcacttt aagccataa | 1239 |

<210> SEQ ID NO 50
<211> LENGTH: 621
<212> TYPE: DNA
<213> ORGANISM: Artificial Sequence
<220> FEATURE:
<223> OTHER INFORMATION: Fusion protein with tropomyosin peptide 1, nt
    sequence

<400> SEQUENCE: 50

| | | |
|---|---|---|
| atgggccatc atcatcatca tcatcatcat catcacagca gcggccatat cgacgacgac | 60 |
| gacaagatgg acgccatcaa gaagaagatg caggctatga agctcgagaa ggacaacgcc | 120 |
| atggacaggg cggatactct cgagcagcag aacaaggagg ccaacaacag ggctgagaag | 180 |
| tccgaggagg aggttttcgg ccttcagaag aagctgcagc agcttgagaa cgacctcgac | 240 |
| agtgtacagg aagctctgct gaaggctaac caacaccttg aggagaagga caaggctctc | 300 |
| cgggctgatg ctgcaccagg agatgcatta cgtttcaaca acattacaa ccacgatctg | 360 |
| aagtttttca ccactccaga taagacaat gatcgatatc cttctgggaa ctgtgggctg | 420 |

```
tactacagtt caggctggtg gtttgatgca tgtctttctg caaacttaaa tggcaaatat      480
tatcaccaaa atacagagg tgtccgtaat gggattttct ggggtacctg gcctggtgta      540
agtgaggcac accctggtgg ctacaagtcc tccttcaaag aggctaagat gatgatcaga      600
cccaagcact ttaagccata a                                                621

<210> SEQ ID NO 51
<211> LENGTH: 564
<212> TYPE: DNA
<213> ORGANISM: Artificial Sequence
<220> FEATURE:
<223> OTHER INFORMATION: Fusion protein with tropomyosin peptide 5, nt
      sequence

<400> SEQUENCE: 51
atgggccatc atcatcatca tcatcatcat catcacagca gcggccatat cgacgacgac       60
gacaagaaga ctctcaccaa caagctgaag gcggctgagg cccgcgctga gttcgctgag      120
agatctgtgc agaagctcca gaaggaggtc gacaggctcg aagacgaact ggttaacgaa      180
aaggagaagt acaagtcaat taccgacgag ctcgaccaga ctttcagcga actgtctggc      240
taccgggctg atgctgcacc aggagatgca ttacgtttca caaacatta caaccacgat      300 ctgaagtttt tcaccactcc agataaagac aatgatcgat atccttctgg aactgtggg     360 ctgtactaca gttcaggctg gtggtttgat gcatgtcttt ctgcaaactt aaatggcaaa      420
tattatcacc aaaaatacag aggtgtccgt aatgggattt tctggggtac ctggcctggt      480
gtaagtgagg cacaccctgg tggctacaag tcctccttca agaggctaa gatgatgatc      540 agacccaagc actttaagcc ataa                                            564

<210> SEQ ID NO 52
<211> LENGTH: 1173
<212> TYPE: DNA
<213> ORGANISM: Artificial Sequence
<220> FEATURE:
<223> OTHER INFORMATION: Fusion proteins with mouse FGL2 peptide:
      Histag-Tropomyosin-linker-mCP

<400> SEQUENCE: 52
atggacgcca tcaagaagaa gatgcaggct atgaagctcg agaaggacaa cgccatggac       60
agggcggata ctctcgagca gcagaacaag gaggccaaca cagggctga agtccgag       120 gaggaggttt tcggccttca gaagaagctg cagcagcttg agaacgacct cgacagtgta      180
caggaagctc tgctgaaggc taaccacac cttgaggaga aggacaaggc tctctctaac      240
gctgagggtg aggttgccgc tcttaaccgt cgcatccagc ttctagagga ggacctcgag      300
aggtctgagg agcgactcaa cactgccacc accaagttgg ccgaggcttc ccaggcagcc      360
gacgagtccg agcgtatgcg caaggtgctc gagaatcgtt ccctctccga cgaggagcgc      420
atggacgccc tcgagaacca actcaaggaa gcccgattcc tggctgaaga agccgacagg      480
aaatacgacg aggtcgcccg taagctggcc atggttgaag ctgatcttga gcagcagag      540 gagcgcgccg agaccggtga atcaaagatc gttgagcttg aggaggagct ccgcgtcgtt      600
ggcaacaacc tgaagtctct cgaagtgtcc gaggagaagg ccaaccagcg tgaagaagcc      660
tacaaggaac agattaagac tctcaccaac aagctgaagg cggctgaggc ccgcgctgag      720
ttcgctgaga gatctgtgca gaagctccag aaggaggtcg acaggctcga agacgaactg      780
gttaacgaaa aggagaagta caagtcaatt accgacgagc tcgaccagac tttcagcgaa      840
ctgtctggct accgggctga tgctgcacca gggatgcct tgcgtttcag tcgacactac      900
```

```
aaccatgacc tgaggttttt cacaacccca gacagagaca acgatcggta cccctctggg      960
aactgtgggc tctattacag ctcaggctgg tggtttgatt catgtctctc tgccaactta     1020
aatggcaaat attaccacca gaaatacaaa ggtgtccgta atgggatttt ctggggcacc     1080
tggcctggta taaaccaggc acagccaggt ggctacaagt cctccttcaa acaggccaag     1140
atgatgatta ggcccaagaa tttcaagcca taa                                 1173
```

FUSION PROTEINS FOR THE TREATMENT OF ALLERGIC DISEASES

TECHNICAL FIELD

The present invention relates to the field of food allergy and particularly to shrimp allergy. Particularly it relates to a fusion protein comprising a first peptide and a second peptide linked together with a linker to be used as a vaccine, means and methods for its preparation and medical uses thereof.

BACKGROUND OF THE INVENTION

Allergic reactions to food represent a major and growing medical, social and economic problem worldwide. Up to 6% of small children and 3 to 4% of the adults have a confirmed allergic reaction to basic foods. Eight types of food account for over 90% of allergic reactions; milk, eggs, peanuts, tree nuts, fish, shellfish, soy and wheat [1, 2]. The clinical reactions of allergy vary from minor oral reactions with itch and mucosal swelling, to urticaria and angioedema, gastrointestinal symptoms, asthma and anaphylaxis with possible fatal result [3]. The economic costs of allergy in the USA alone are estimated to be USD 14.5 billion per year, with food allergies costing USD 500 million per year [4].

Shellfish allergy is a potentially life-threatening disease that is seldom outgrown [1; 2] and, in some parts of the world, the most common food allergy among adults [3]. Among crustaceans, such as shrimp, crab, crawfish and lobster, shrimp is frequently identified as a cause of IgE mediated adverse reactions in food allergic individuals. Although exact numbers on the prevalence of shrimp allergy are lacking, estimations have ranged from 0.6 to 2.8% in food allergic individuals [5, 6]. The shellfish species that most frequently elicit food-allergic reactions belong to the taxonomic class Crustacea that includes shrimp, crab, crawfish and lobster. Affected individuals usually display allergic reactivity to multiple crustacean species. Molecular and clinical cross-reactivity was reported between crustaceans and other invertebrate foods such as mussels, oyster, squid and octopus, but also to invertebrate aeroallergens such as house dust mite and cockroaches (Reviewed by Lopata et al., 2010) [1].

The presence of a heat-stable allergen in shellfish was first identified in shrimp by Hoffman et al. (1981) [4] and this allergen was later identified as the muscle protein tropomyosin [5-7]. More than 80% of shrimp-allergic individuals were reported to have serum IgE against shrimp tropomyosin [6; 8-10]. The amino acid sequence of invertebrate tropomyosins is highly conserved, with 95% identity between shrimp and Storage mite (*Tyrophagus putrescentiae*). Tropomyosin was found to play an important role in the cross-reactivity seen between the different invertebrate species—suggesting tropomyosin to be an invertebrate pan-allergen [1].

The most common control of food allergy is merely avoidance of the relevant offending allergen, i.e. no vaccine is available for the treatment of food allergy. For venom and inhalant allergies, and grass and birch in particular, desensitisation and tolerance development has been carried out for almost 100 years as subcutaneous or recently sub-lingual immunotherapy (SCIT and SLIT, respectively) [7]. Treatment involves increasing doses of standardised allergen extracts until a maintenance dose is reached; this dose is injected approximately every second month for 3-5 years. Alternative strategies are currently being tried out, such as intra-lymphatic injections, which may considerably shorten the time of treatment, but such treatment is experimental at present [8]. Due to safety reasons, tolerance induction in the form of SCIT has been abandoned in food allergic patients.

Another treatment that is used today is Omalizumab (trade name XOLAIR®, Roche/Genentech and Novartis) which is an injectable, prescription medicine approved for patients 12 years and older with moderate to severe allergic asthma in the United States and with severe, persistent allergic asthma in many other countries. It is a recombinant DNA-derived humanized monoclonal antibody and exerts its action by binding to circulating IgE, reducing IgE receptor expression, and decreasing mediator release from mast cells and basophils [9]. Omalizumab has also been studied in combination with allergen-based SIT for the purpose of reducing anaphylactic reactions and to achieve therapeutic effects in shorter treatment periods. However, Omalizumab does not comprise allergen specific immunotherapy as opposed to the presently proposed invention.

Fibrinogen-like protein 2 (FGL2), also known as fibroleukin, is a 70-kDa glycoprotein that belongs to the fibrinogen-related superfamily of proteins [10]. It is expressed on the surface of macrophages, T cells and endothelial cells and exerts in that form (as a transmembrane protein) prothrombinase activity [11]. The prothrombinase activity of FGL2 has been associated with several diseases such as hepatitis and abortion [12]. However, as a soluble protein FGL2 lacks prothrombinase activity has instead been associated with immune-suppression by binding to the inhibitory receptor FcgammaRIIb (FcγRIIb) [13] that is highly expressed on the cell-surface of B-cells and basophils/mast cells. Soluble FGL2 is secreted mainly by memory T-cells and was recently presented as a marker for tolerance induction [14].

Human basophils express high-affinity IgE receptors (Fcepsilon RI, FcεRI). FcεRI is associated with two immunoreceptor tyrosine-based activation motifs (ITAM) that are activated upon FcεRI aggregation, when specific antigens (Ag) binds to receptor-bound IgE antibodies. Activated basophils release vasoactive mediators and cytokines that promote allergic inflammation [15].

Human and mouse mast cells, basophils and B-cells express the inhibitory receptor FcγRIIb on the cell surface [16, 17]. FcγRIIb is an immunoreceptor tyrosine-based inhibition motif (ITIM) containing inhibitory receptor. Co-engagement of FcγRIIb with FcεRI on basophils [16] and mast cells [18] inhibits IgE induced activation of these cells. Furthermore, co-engagement of FcγRIIb and B-cell receptor complex has been shown to supress ex-vivo B-cell activation and humoral responses in vivo [19].

WO 97/07218 describes fusion proteins comprising one or more antigens and one or more moieties interacting with human FcγRII. The invention relates to complexes of human IgG and antigen/allergen and concerns fusion proteins between anti-CD32 molecules and antigen/allergen.

U.S. Pat. No. 7,632,495 B2 and US2010/0048486 A1 describes methods and compositions for inducing immune suppression in graft rejection and autoimmune diseases by administering an effective amount of a soluble FGL2 protein or a nucleic acid encoding a soluble fgl2 protein.

U.S. Pat. No. 7,655,229 B2 describes antibodies that selectively bind human FcγRIIb, with little or no binding to other human FcgammaRs. The inventions provides isolated bispecific antibodies comprising an antibody that selectively binds FcγRIIb, and a second antibody that specifically binds an activating receptor for inhibiting immune responses and suppressing histamine release.

US2006/0171942 describes fusion molecules comprising an Fcε fragment sequence including functionally active CH2, CH3 and CH4 domains of the constant region of an IgE heavy chain linked at its C-terminus to the N-terminus of a second polypeptide including functionally active hinge, CH2 and CH3 domains of the constant region of an IgG1 heavy chain for the treatment of allergic disease.

There is thus an urgent need to develop means and methods for a vaccine against food allergy such as shrimp allergy. Accordingly, the present invention provides means and methods to address such needs and interests for food allergy, and particularly shrimp allergy.

SUMMARY OF THE INVENTION

The present invention relates to fusion proteins between an allergen and a C-terminal FGL2 peptide.

In one aspect the present invention relates to a fusion protein comprising a first peptide and a second peptide linked together with a linker, wherein the first peptide is an allergen and the second peptide is a targeting unit and the second targeting unit peptide is a FGL-2 C-terminal peptide according to SEQ ID no 1 or its nucleotide sequence thereof according to SEQ ID no 47. In further embodiments, said fusion protein is wherein the first allergen peptide is shrimp tropomyosin Pan b 1 according to SEQ ID no 15 or parts or fragments thereof. In still further embodiments, the fusion protein is wherein parts or fragments of Shrimp tropomyosin comprises the sequence according to any of SEQ ID no 4, 5, 6, 7, and 8.

In a further embodiment, the fusion protein is wherein the allergen unit is P5 (SEQ ID no 8) and the targeting unit is a FGL-2 C-terminal peptide according to SEQ ID no 1. In still another embodiment, the fusion protein is wherein the allergen unit is P1 (SEQ ID no 4) and the targeting unit is a FGL-2 C-terminal peptide according to SEQ ID no1.

Further, the fusion protein may comprise a linker. In further embodiments, said fusion protein as described in any embodiment herein is wherein said linker is RADAAP (SEQ ID no 12). Thus, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1.

Accordingly, said fusion protein may in still further embodiments be wherein the allergen unit is P5 (SEQ ID no 8), the targeting unit is a FGL-2 C-terminal peptide according to SEQ ID no 1 and the linker is RADAAP (SEQ ID no 12). In still further embodiments, the fusion protein is wherein the allergen unit is P1 (SEQ ID no 4), the targeting unit is a FGL-2 C-terminal peptide according to SEQ ID no 1 and the linker is RADAAP (SEQ ID no 12).

A further aspect of the present invention is a fusion protein according to any embodiments herein for medical use.

Still further aspects are use of a fusion protein according to any of the embodiments herein in the manufacture of a medicament for the treatment and/or prevention of shrimp allergy.

Still even further aspects are fusion proteins according to any of the embodiments herein for use in the treatment and/or prevention of shrimp allergy. Aspects also include a fusion protein according to all embodiments herein for use as a vaccine as well as a vaccine composition comprising the fusion protein according to any embodiment provided herein.

Another aspect of the present invention includes methods for preparing a fusion protein according to any embodiment provided herein comprising the steps of:

a) providing an isolated first allergen peptide from pan b 1 (SEQ ID no 15) or its nucleotide sequence thereof (SEQ ID no 43),
b) providing an isolated second targeting unit peptide or its nucleotide sequence thereof, and wherein the second targeting unit peptide is a FGL-2 C-terminal peptide according to SEQ ID no 1 or its nucleotide sequence according to SEQ ID no 47,
c) optionally providing a linker,
d) fusing the isolated first allergen peptide or its nucleotide sequence thereof in a) above, an isolated second targeting unit peptide or its nucleotide sequence thereof, and optionally the linker in c) and wherein the second targeting unit peptide is a FGL-2 C-terminal peptide according to SEQ ID no 1 in b) above, and
e) optionally isolation of said fusion protein.

Further embodiments of the method are wherein said isolated first allergen peptide from pan b 1 is any of the peptides P1 (SEQ ID no 4), P2 (SEQ ID no 5), P3 (SEQ ID no 6), P4 (SEQ ID no 7) or P5 (SEQ ID no 8). Still even further embodiments of the methods in all its provided embodiments are wherein the linker is RADAAP (SEQ ID no 12) or its nucleotide sequence according to SEQ ID no 46. Still even further embodiments are wherein said fusion protein is isolated. Suitable means for isolation herein are given and one example is a histidin-tag according to its sequence provided in SEQ ID no 9 or its nucleotide sequence provided in SEQ ID no 45. Said histidin-tag is usable for all embodiments of the fusion protein or peptides provided herein as exemplified e.g in the examples.

Further aspects include a method for inhibiting, preventing and/or treating shrimp allergy, comprising administering an effective amount of a fusion protein according to any of the embodiments provided herein or a vaccine composition as provided herein to a mammal e.g. a human.

Still further aspects include use of a fusion protein according to any embodiments provided herein or a vaccine composition as provided herein in the vaccination of a mammal, such as a human, for the treatment and/or prevention of shrimp allergy.

Still even further aspects include a vaccine composition as provided herein in all its embodiments for use in the treatment and/or prevention of shrimp allergy. Still even a further aspect includes a kit of parts comprising the fusion protein according to any of the embodiments provided herein or a vaccine composition as provided herein in all its embodiments, a container comprising said fusion protein and optionally instructions for its use.

BRIEF DESCRIPTION OF THE DRAWINGS

FIG. 1A shows a schematic overview of the design of the soluble human FGL2 C-terminal peptide (CP) in comparison to the whole human FGL2 protein. On top whole hFGL2 is given (black). The region responsible for prothrombinase activity according to Chan et al. [11] is indicated (brick pattern). The N-terminal histidin-tag added to CP is indicated (white). FIG. 1B shows the amino acid sequence of CP, including the histidin-tag (bold) on the N-terminal end of the protein (SEQ ID no 1). The peptides that have been confirmed by MS-analyses are marked (underlined). The protein has a predicted size of 14.2 kDa.

FIG. 2 shows the generation of CP in an *E. coli* expression system. SDS-PAGE followed by Coomassie blue staining of proteins purified by immobilized metal affinity chromatography (IMAC) and dialysis as described in "Materials and Methods" demonstrates a dominant band of approximately 15 kDa. An additional weaker band of approximately 30 kDa indicates dimerization of the protein. Protein sizes (kDa) are indicated on the left side of the gel.

FIG. 3A, FIG. 3B, and FIG. 3C show the binding his-tagged CP (10 μM) to CD20+ human B-cells from three healthy individuals (A, B and C) after 30 minutes of incubation. Binding was analysed by flow cytometry; gated B-cells were plotted against the intensity of binding of his-tagged proteins (FL-4). The black curve represents binding of CP, the white curves represent binding of control protein (recombinant shrimp tropomyosin Pan b 1, rT) or sample without added proteins. The two controls are nearly identical. The high intensity of binding of CP shows that the protein binds to human B-cells.

FIG. 4A shows a schematic overview of the fusion protein consisting of an N-terminal His-tag (white), shrimp tropomyosin (diagonally striped), a linker (horizontally striped) and CP (black). This protein is called FP. FIG. 4B shows the aminoacid sequence of FP (SEQ ID no 2). The peptides that have been confirmed by MS-analyses are underlined. The histidin-tag and linker (RADAAP) are in bold text. The predicted size of the protein is 47.6 kDa.

Figure 5:
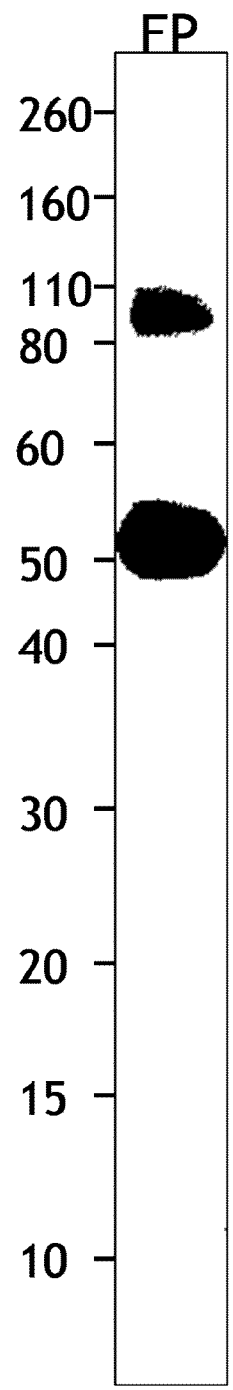

FIG. 5 shows the generation of FP in an *E. coli* expression system. SDS-PAGE followed by Coomassie blue staining of FP purified by IMAC. Protein sizes (kDa) are indicated on the left side of the gel. 2 μg protein was loaded. FP appears as a protein of approximately 50 kDa. An additional band of approximately 100 kDa was seen, which indicates dimerization of FP.

Figure 6:

FIG. 6 shows a proposed dimeric structure of FP including the histidin-tags (white boxes), tropomyosin coiled-coil alpha-helix (coils), the linkers (striped boxes) and CP (black balloons).

FIG. 7 shows the amino acid sequence of whole shrimp tropomyosin (Pan b 1, SEQ ID no 15) and position of the five constructed peptides thereof (SEQ ID no 4-8). The N-terminal His-tag (SEQ ID no 9) common for all the five peptides and whole rPan b 1 is not shown. T, whole tropomyosin (Pan b 1); P1-5 tropomyosin peptides 1-5.

FIG. 8A shows a schematic overview of a FP containing a truncated shrimp allergen. The protein consists of an N-terminal His-tag (white), a shrimp tropomyosin-peptide (one of P1-5, diagonally striped), a linker (horizontally striped) and CP (black). FIG. 8B shows the aminoacid sequence of shortened FP containing shrimp tropomyosin P1, called FP1 (SEQ ID no 10). The predicted size of the protein is 23.9 kDa. FIG. 8C shows the aminoacid sequence of shortened FP containing a shrimp-tropomyosin P5, called FP5 (SEQ ID no 11). The predicted size of the protein is 21.7 kDa. The histidin-tag and linker (RADAAP) are in bold text.

Figure 9:
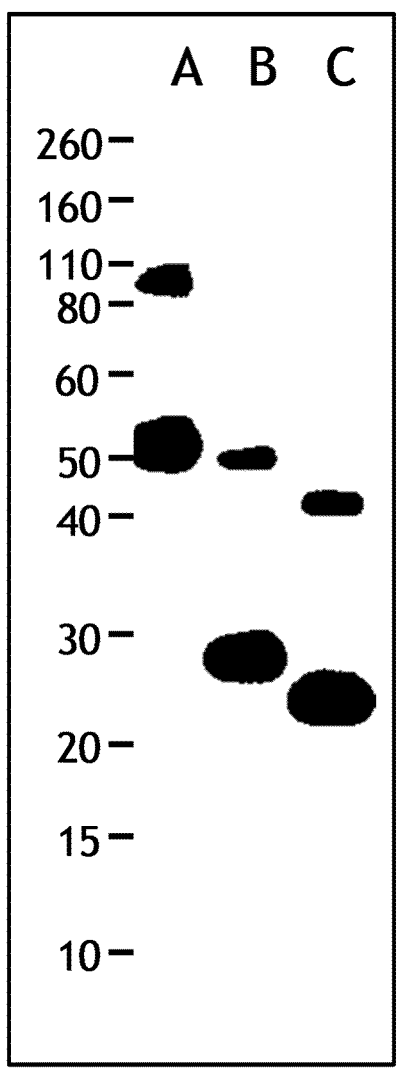

FIG. 9 shows the generation the FP1 (B) and FP5 (C). FP is also shown (A). The proteins were produced in an *E. coli* expression system. Shown is SDS-PAGE followed by Coomassie blue staining of FP purified by IMAC. Protein sizes (kDa) are indicated on the left side of the gel. 5 μg protein was loaded. The analysis demonstrates a proteins of approximately 26 kDa (B, FP1), of approximately 24 kDa (C, FP5), of approximately 50 kDa (A, FP). In addition proteins of approximately 100, 50 and 45 kDa are present, which indicates dimerization of A, B and C, respectively.

Figure 10:
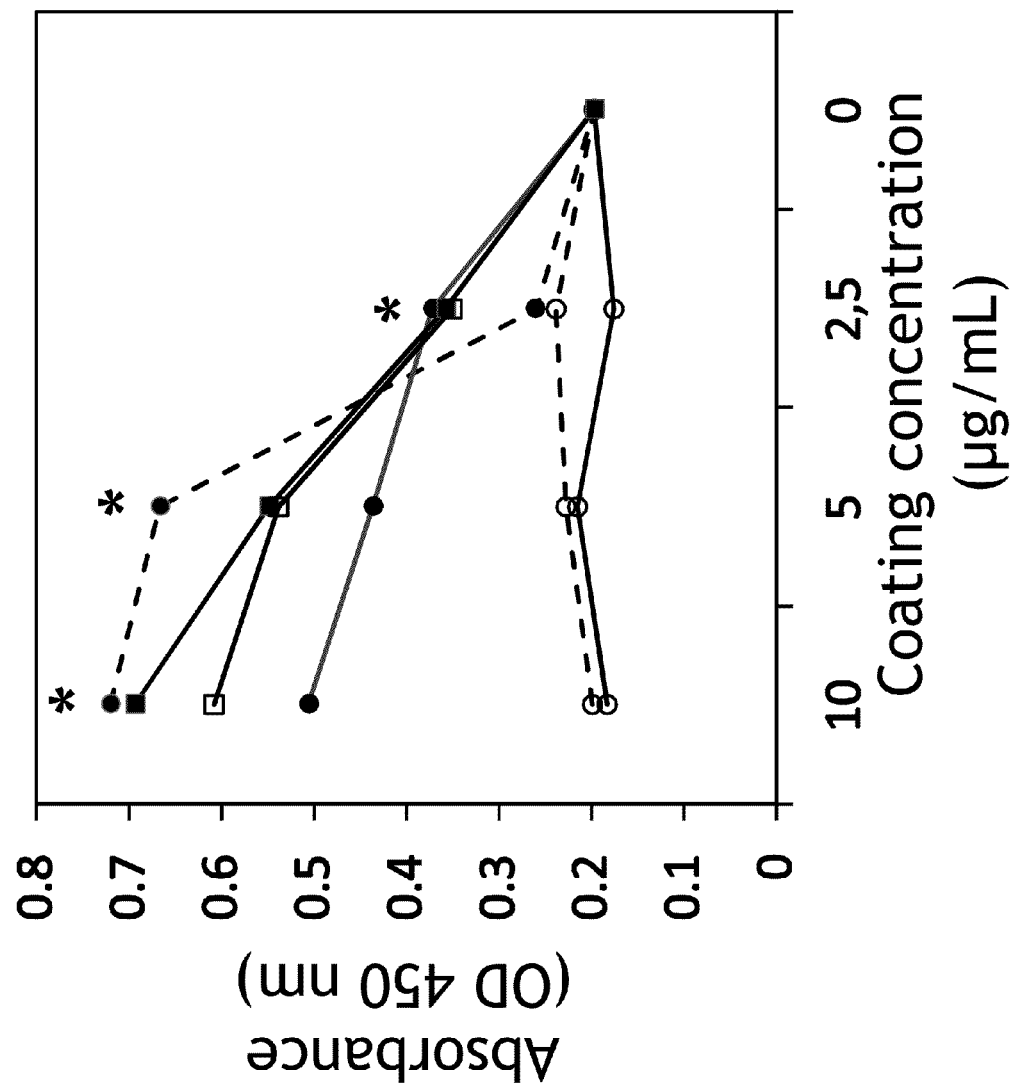

FIG. 10 shows the binding of proteins containing CP to FcγRIIb in ELISA. Proteins containing CP or a control protein, human serum albumin, were immobilized to the surface of the ELISA wells and binding of added soluble recombinant FcγRIIb was analysed. The following proteins were included in the assay: CP (broken line, filled circles), FP (solid line, filled circles), FP1 (solid line, open squares), FP5 (solid line, filled squares), control protein (broken line, open circles) and no protein coated (solid line, open rounds). * Indicates that proteins containing CP (CP, FP, FP1 and FP5) are significantly different from the controls at 2.5, 5 and 10 μg/mL (two sided Student's t-test, equal variances).

Figure 11:
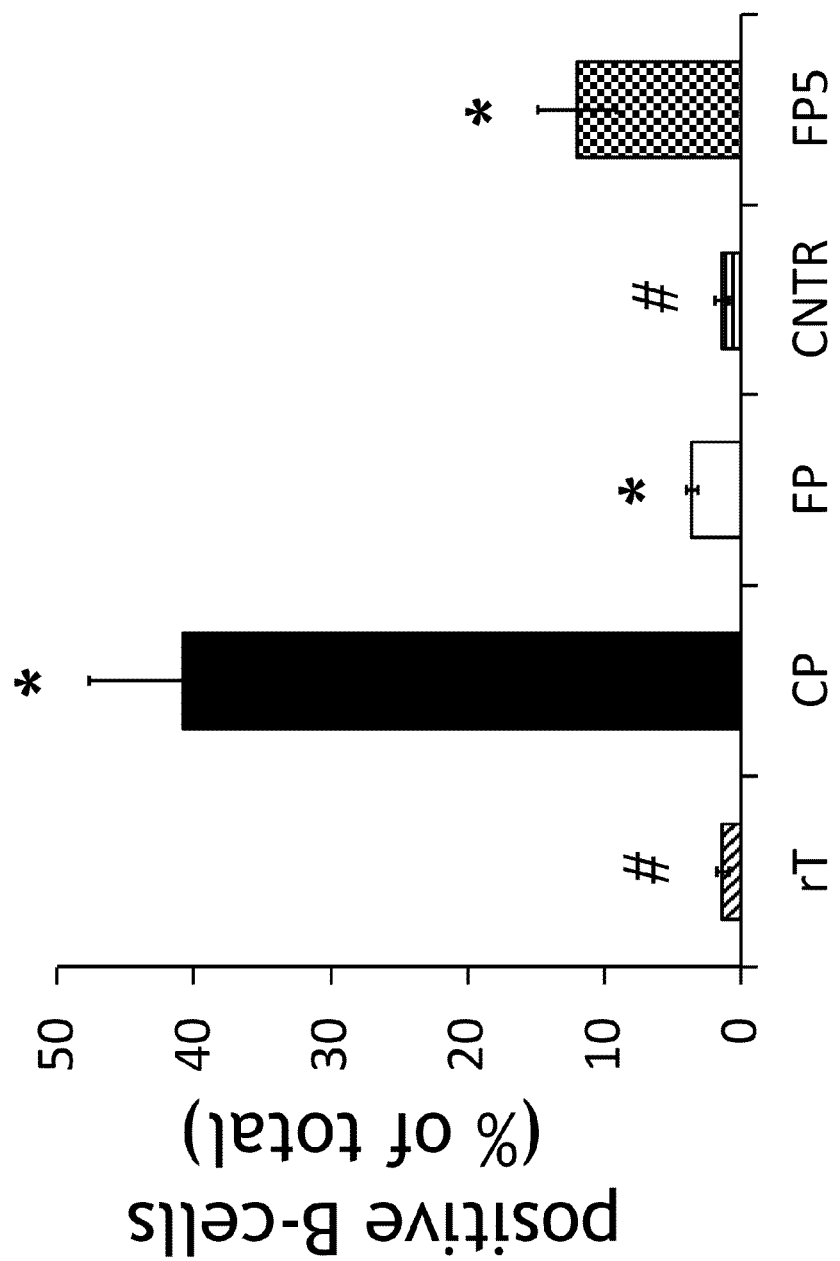

FIG. 11 shows binding of recombinant shrimp tropomyosin (rT, diagonal stripes), CP (black), FP (white), control protein recombinant CD16 (horizontally striped), and FP5 (blocked) to B-cells of four shrimp allergic individuals after 30 minutes of incubation with the proteins (10 μg/mL, see methods section). The figure shows percentages B-cells of the total number of B cells (mean±standard error of the mean). # Indicates that rT and control are not statistically different, * Indicates that CP, FP and FP5 are different from control incubations (rT and CNTR), and each other (two tailed Student's t-test, equal variances).

FIG. 12A, FIG. 12B, and FIG. 12C show that FP (white) induces a lower percentage of human basophils from three shrimp allergic patients (A-C) than recombinant tropomyosin (diagonal stripes) at concentrations 0.1 μg and 0.01 μg (A and B), or from 300 nM and lower in vitro (C). CCR2-positive basophils were gated and CD63-expression on the cell surface indicates activation of these cells. See methods section for details. The bars demonstrate percentages activated basophils of the total number of basophils.

Figure 13:
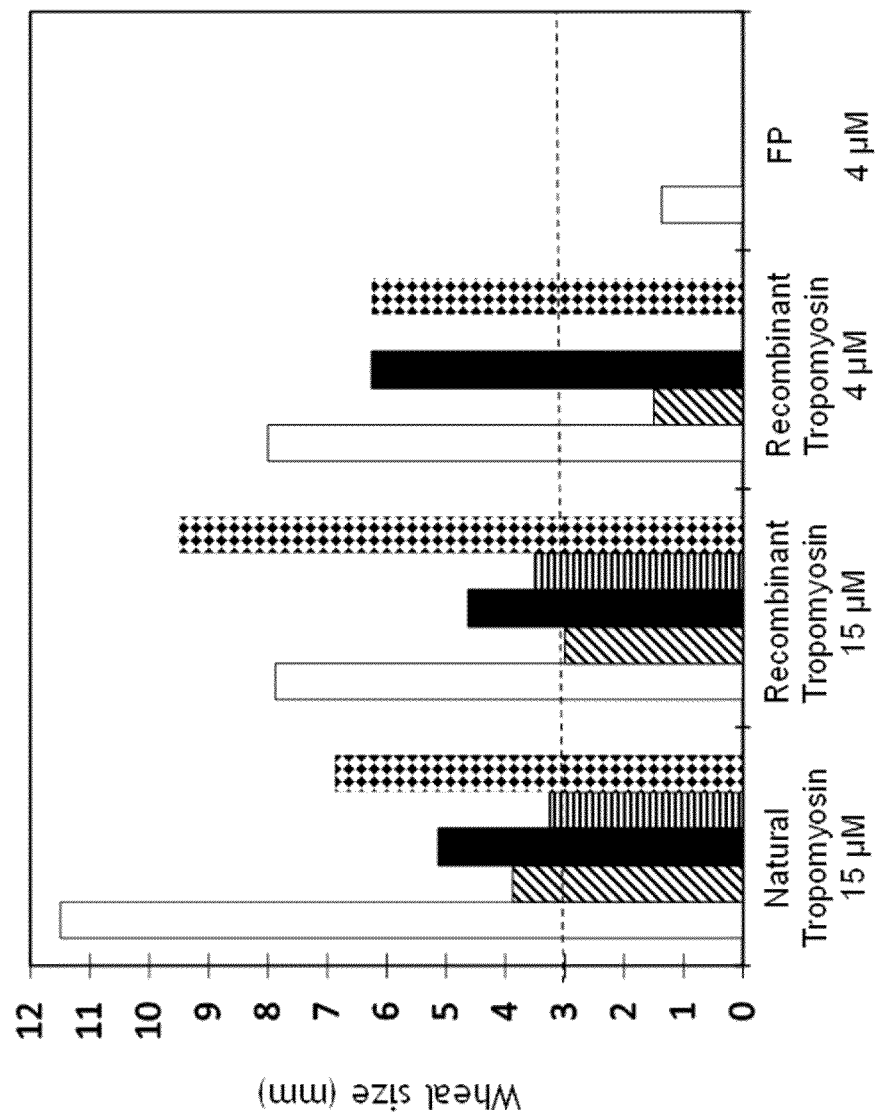

FIG. 13 shows that FP fails to induce activation of human mast cells. Human skin prick tests of shrimp allergic patients with natural tropomyosin (15 μM), recombinant tropomyosin (15 and 4 μM) and FP (4 μM) were tested. A nearby absence of reactivity was observed towards FP, while responses were observed towards a similar molar amount of recombinant tropomyosin. Hence, responses above 3 mm are regarded positive responses. The results show skin prick tests of five shrimp allergic individuals; patient A (open bars), patient B (striped bars), patient C (black bars), patient D (horizontally striped bars) and patient E (brick bars).

FIG. 14 shows the amino-acid sequence of the murine homologue of CP (mCP), including a N-terminal histidin-tag (bold) (SEQ ID no 13). The protein has a predicted size of 14.3 kDa.

Figure 15:
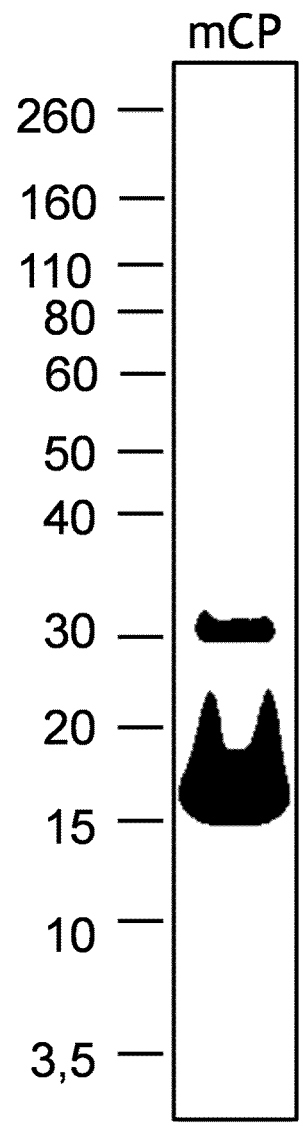

FIG. 15 shows the generation of mCP in an *E. coli* expression system. SDS-PAGE followed by Coomassie blue staining of proteins purified by immobilized metal affinity chromatography (IMAC) as described in "Materials and Methods". mCP appears of a protein of approximately 15 kDa. An additional protein of approximately 30 kDa was observed, which indicated dimerization of mCP. Protein sizes (kDa) are indicated on the left side of the gel. 20 μg mCP was loaded.

FIG. 16A shows a schematic overview of the fusion protein consisting of an N-terminal His-tag, shrimp tropomyosin, a linker (RADAAP) and mCP (SEQ ID no 14). This protein is called mFP. FIG. 16B shows the amino acid sequence of mFP. The predicted size of mFP is 47.76 kDa.

Figure 17:
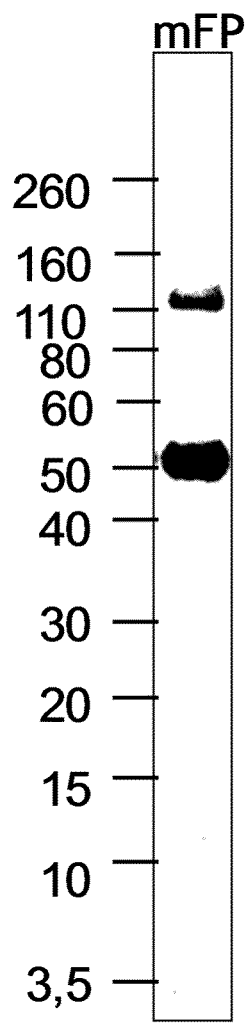

FIG. 17 shows the generation of soluble mFP in an *E. coli* expression system. SDS-PAGE followed by Coomassie blue staining of mFP purified by IMAC. Protein sizes (kDa) are indicated on the left side of the gel. 2 μg of mFP was loaded. mFP appears as a protein of approximately 50 kDa. An additional band of approximately 100 kDa indicates dimerization of mFP.

Figure 18:
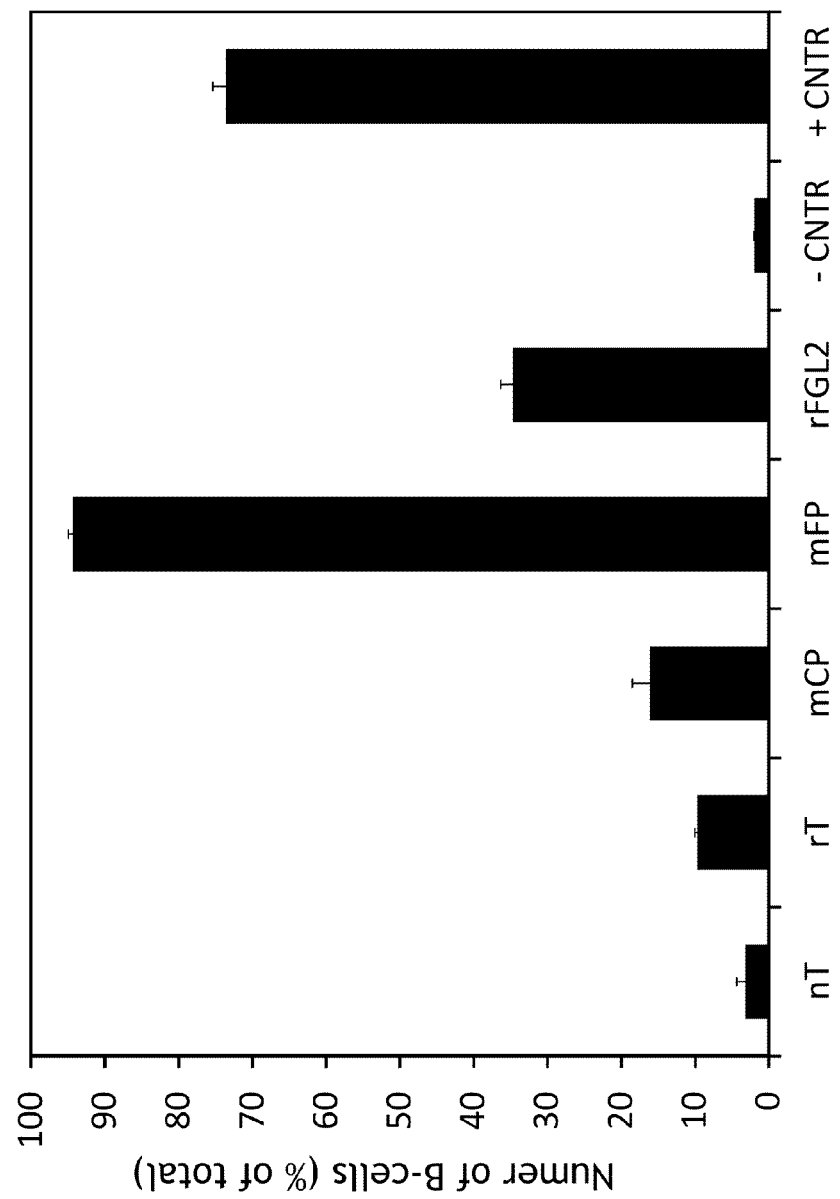

FIG. 18 shows that mFP binds a high number of mouse B-cells from shrimp tropomyosin sensitized mice. Bars represent the percentage of total B-cells±SD of two separate readings. Mouse splenocytes were incubated with the different proteins indicated in the figure (200 μM) for 4 hours at 37° C. Binding of his-tagged proteins was investigated by flow cytometry using anti-CD19 PE as a positive marker for murine B-cells and anti-his Alexa 647 to stain his-tagged protein on cell surface. nT: natural tropomyosin Pan b 1; rT:

recombinant tropomyosin Pan b 1; mCP: mouse CP; mFP: murinized FP; rFGL2: recombinant mouse FGL2; −CNTR; no protein added; +CNTR; anti-mouse FcγRIIb.

Figure 19:
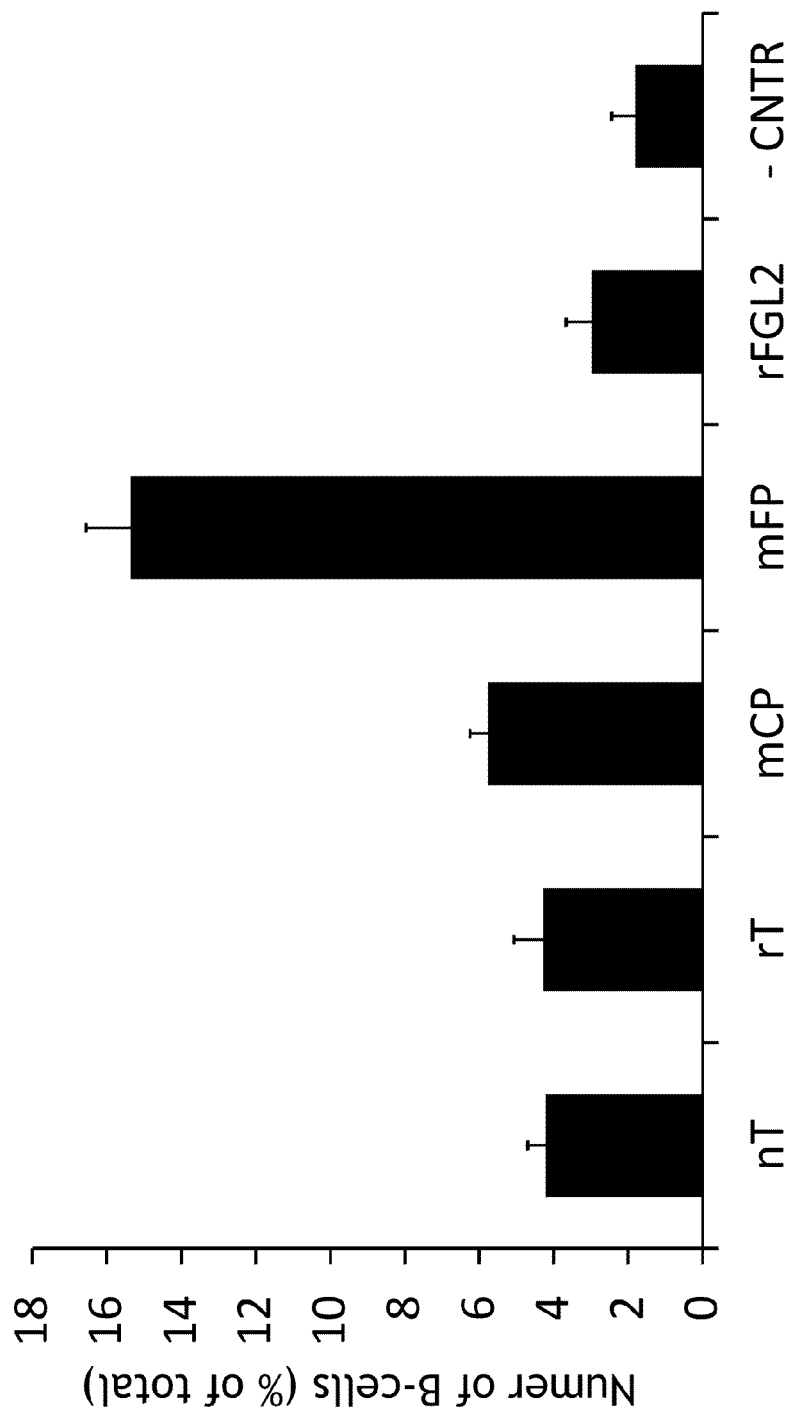

FIG. 19 shows that mFP induces apoptosis of in CD19$^+$-B-cells from shrimp tropomyosin sensitized mice after ex-vivo stimulation for 4 hours at 37° C. Bars represent the percentage of total B-cells±SD of two separate readings. The concentration of the proteins was 200 μM. Annexin-V surface expression as a marker for apoptosis was investigated by flow cytometry. nT: natural tropomyosin Pan b 1; rT: recombinant tropomyosin Pan b 1; mCP: mouse CP; mFP: murinized FP; rFGL2: recombinant mouse FGL2; −CNTR; no protein added.

Figure 20:
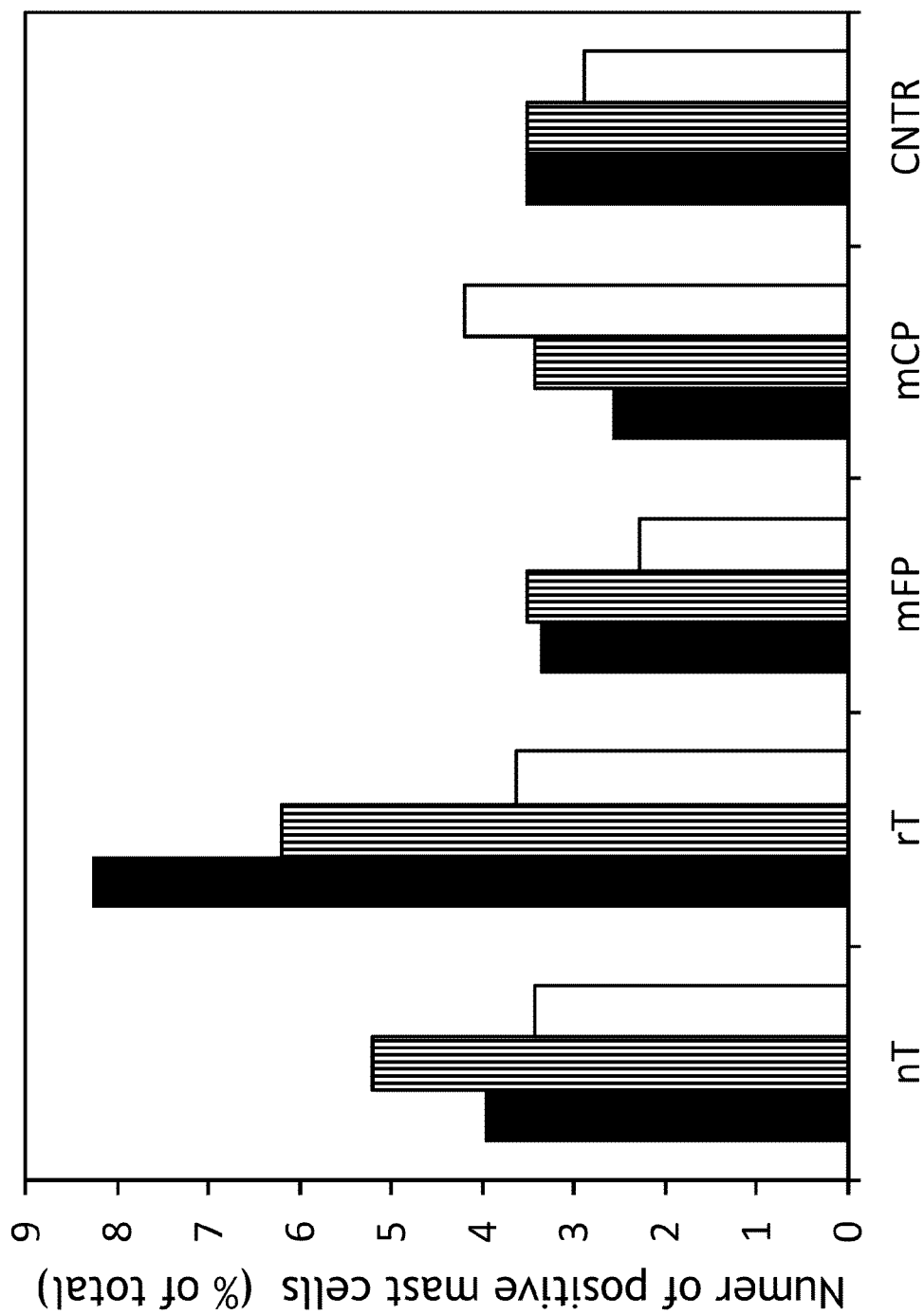

FIG. 20 shows absence of activation of peritoneal mast cells from shrimp tropomyosin sensitized mice after incubation with mFP for 2 hours at 37° C. in contrast to a similar molar amount of recombinant allergen (rT) that showed positive responses at 50 μM (black bars) and 10 μM (striped bars). Protein concentrations added of 2 μM are shown as open bars. Activation of mast cells was investigated by measuring upregulation of CD200R expression on the cell surface (see methods section for more information). Percentages above 5% are regarded positive. nT: natural tropomyosin Pan b 1; rT: recombinant tropomyosin Pan b 1; mFP: mouse FP; mCP: mouse CP; —CNTR; no protein added.

FIG. 21 shows an overview of the patients that participated. The patients are adults with a well-defined shrimp allergy.

DETAILED DESCRIPTION

LIST OF ABBREVIATIONS

CNTR control
CP human FGL2 C-terminal peptide
FGL2 Fibrinogen like protein 2
FP fusion protein of shrimp tropomyosin, linker, and CP
FP1 fusion protein of P1, linker, and CP
FP5 fusion protein of P5, linker, and CP
IMAC immobilized metal affinity chromatography
ITAM immunoreceptor tyrosine-based activation motif
ITIM immunoreceptor tyrosine-based inhibition motif
mCP murine FGL2 C-terminal peptide
mFP fusion protein of shrimp tropomyosin, linker, and mCP
nT natural shrimp tropomyosin (Pan b 1)
rT recombinant shrimp tropomyosin (Pan b 1)
P1-5 shrimp tropomyosin peptides 1-5

DEFINITIONS

As used herein, FGL2 is intended to mean fibrinogen-like protein-2, or fibroleukin.

As used herein, the term "peptide", "polypeptide", or "protein" in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme motif covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, linkers, formation of cystine, formation of pyroglutamate, formylation, gammacarboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., *Proteins—Structure And Molecular Properties,* 2nd Ed., W. H. Freeman and Company, New York (1993); Wold, F., "Posttranslational Protein Modifications: Perspectives and Prospects," in *Posttranslational Covalent Modification of Proteins,* Johnson, B. C., ed., Academic Press, New York (1983), pp. 1-12; Seifter et al., "Analysis for protein modifications and nonprotein cofactors," Meth. *Enqmol.* 182:626-646 (1990), and Rattan et al., *Ann. N.Y. Acad. Sci.* 663:48-62 (1992).

As used herein, amino acids are represented by their common one or three-letter codes, as is common practice in the art. Accordingly, the designations of the twenty naturally occurring amino acids are as follows: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline-Pro (P); Serine=Ser (S); Threonine=Thr (T); Tryptophan=Trp (W); Tyrosine=Tyr (Y); Valine=Val (V). The polypeptides herein may include all L-amino acids, all D-amino acids or a mixture thereof. The polypeptides comprised entirely of D-amino acids may be advantageous in that they are expected to be resistant to proteases naturally found within the human body, and may have longer half-lives.

As used herein the terms "fragment", "portion" and "part," as used interchangeably herein, refer to any composition of matter that is smaller than the whole of the composition of matter from which it is derived. For example, a portion of a polypeptide may range in size from two amino acid residues to the entire amino acid sequence minus one amino acid. However, in most cases, it is desirable for a "portion" or "fragment" to retain an activity or quality which is essential for its intended use. For example, useful portions of an antigen are those portions that retain an epitope determinant.

As used herein, the terms "complement" "complementarity" or "complementary" as used herein, are used to describe single-stranded polynucleotides related by the rules of anti-parallel base-pairing. For example, the sequence 5'-CTAGT-3' is completely complementary to the sequence 5'ACTAG-3'. Complementarity may be "partial" where the base pairing is less than 100%, or complementarity may be "complete" or "total," implying perfect 100% antiparallel complementation between the two polynucleotides. By convention in the art, single-stranded nucleic acid molecules are written with their 5' ends to the left, and their 3' ends to the right.

As used herein, "sequence identity" means the percentage of amino acid residues in a candidate sequence that is identical with the amino acid residues in a reference polypeptide sequence (e.g., a native polypeptide sequence), after aligning the sequences and introducing gaps, if necessary, to achieve the maximum percent sequence identity. The % sequence identity values can be generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1. If nothing else is stated, the sequences herein in all its embodiments encompass sequences with 90, 95, 97, 98 or even 99% identity to the sequences given herein while remaining its biological activity or function such as receptor binding capacity.

As used herein, the term "allergen," and grammatical variants thereof, are used to refer to special antigens that are capable of inducing IgE-mediated allergies. An allergen can be almost anything that acts as an antigen and stimulates an IgE-mediated allergic reaction. Common allergens can be found, for example, in food, such as shrimp, pollen, mold, house dust which may contain mites as well as dander from house pets, venom from insects such as bees, wasps and mosquitoes. Allergens as used herein are defined as antigens to which atopic patients respond with allergic reactions e.g. shrimp tropomyosin in the case of shrimp allergy.

The term "antigen," as used herein, refers to any agent that is recognized by an antibody, while the term "immunogen" refers to any agent that can elicit an immunological response in a subject. The terms "antigen" and "immunogen" both encompass, but are not limited to, polypeptides. In most, but not all cases, antigens are also immunogens.

Allergy as defined herein is a disease in which IgE antibodies mediate activator of effector cells, such as mast cells and basophils, by binding to the high affinity IgE receptor FcεRI (Fc epsilon receptor I).

As used herein, the terms "vaccine therapy", "vaccination" and "vaccination therapy," as used interchangeably herein, refer in general to any method resulting in immunological prophylaxis. In one aspect, vaccine therapy induces an immune response, and thus long-acting immunity, to a specific antigen. These methods generally entail the delivery to a subject of an immunogenic material to induce immunity. In this case, the immunogenic material is generally killed microbes of virulent strains or living, attenuated strains, or derivatives or products of virulent pathogens. In another aspect, the "vaccine therapy" refers to a method for the downregulation of an immune potential to a particular antigen (e.g., to suppress an allergic response). This type of vaccine therapy is also referred to as "tolerance therapy." Vaccine therapies typically entail a series of parenteral or oral administrations of the immunogenic material over an extended period of time.

As used herein, the terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. In one embodiment the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

As used herein, a "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

As used herein, the term "promoter" means a nucleotide sequence that, when operably linked to a DNA sequence of interest, promotes transcription of that DNA sequence. For example, nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

As used herein, the terms "treat" or "treatment" refer to both therapeutic treatment and prophylactic or preventative measures, wherein the object is to prevent or slow down or lessen an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

As used herein "chronic" administration refers to administration of the agent(s) in a continuous mode as opposed to an acute mode, so as to maintain a desired effect or level of agent(s) for an extended period of time.

As used herein "intermittent" administration is treatment that is not consecutively done without interruption, but rather is periodic in nature.

As used herein, administration "in combination with" one or more further therapeutic agents includes simultaneous (concurrent) and consecutive administration in any order.

As used herein "effective amount" is an amount sufficient to effect beneficial or desired therapeutic including preventative results. An effective amount can be administered in one or more administrations.

As used herein "carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counter ions such as sodium; and/or nonionic surfactants such as TWEEN®, polyethylene glycol (PEG), and PLURONICS™.

As used herein, the term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. In one embodiment the mammal is human.

As used herein, the terms "subject" or "patient" are used interchangeably, and can refer to any animal, and in one embodiment a mammal, that is the subject of an examination, treatment, analysis, test or diagnosis. In one embodiment, humans are the subject. A subject or patient may or may not have a disease or other pathological condition.

It is an objective of the present invention to provide means and methods to prevent food allergy and specifically shrimp allergy.

The vaccine against shrimp-allergy as described herein is a bi-specific fusion protein consisting of a major allergen of shrimp linked to a functional domain of a human ligand (described below). Fusion proteins or chimeric proteins are proteins created through the joining of two or more genes which originally codes for separate proteins (by recombinant DNA technology). The two proteins are fused together by a short linker to allow the proteins to fold correctly and to exert their effects. An N-terminal His-tag may optionally be added to allow purification of the vaccine. Since tropomyosin spontaneously dimerizes, the vaccine protein will be dimeric as indicated in FIG. 6.

Fibrinogen-like protein 2 (FGL2), also known as fibroleukin, is a 70-kDa glycoprotein that belongs to the fibrinogen-related superfamily of proteins [10]. It is expressed on the surface of macrophages, T cells and endothelial cells and exerts in that form (as a transmembrane protein) prothrombinase activity [11]. The prothrombinase activity of FGL2 has been associated with several diseases such as hepatitis and abortion [12]. However, as a soluble protein FGL2 lacks prothrombinase activity has instead been associated with immune-suppression by binding to the inhibitory receptor FcγRIIb [13] that is highly expressed on the cell-surface of B-cells and basophils/mast cells. Soluble FGL2 is secreted mainly by memory T-cells and was recently presented as a marker for tolerance induction[14].

Human basophils express high-affinity IgE receptors (Fcepsilon RI, FcεRI). FcεRI is associated with two ITAM that are activated upon FcεRI aggregation, when specific antigens (Ag) bind to receptor-bound IgE antibodies. Activated basophils release vasoactive mediators and cytokines that promote allergic inflammation [15].

Human and mouse mast cells, basophils and B-cells express the inhibitory receptor FcγRIIb on the cell surface [16]. FcγRIIb is an ITIM containing inhibitory receptor [17]. Co-engagement of FcγRIIb with FcεRI on basophils [16] and mast cells [18] inhibits IgE induced activation of these cells. Furthermore, co-engagement of FcγRIIb and B-cell receptor complex has been shown to supress ex-vivo B-cell activation and humoral responses in vivo [19].

The Fusion Protein

Thus, the present invention provides a fusion protein comprising a first protein and a second protein linked together with a linker, wherein the first protein is an allergen and the second peptide is a targeting unit and the second targeting unit peptide is a FGL-2 C-terminal peptide according to SEQ ID no 1.

Further, the fusion protein is wherein the first allergen peptide. Pan b 1 is given in amino acids in SEQ ID no 15 and as nucleotide sequence in SEQ ID no 43. Particularly, said fusion protein is wherein parts and fragments of Shrimp tropomyosin comprises the sequence according to any of SEQ ID no 4, 5, 6, 7, 8.

In specific embodiments, said fusion protein is wherein the allergen unit P5 (SEQ ID no 8), the targeting unit is a FGL-2 C-terminal peptide according to SEQ ID no 1 or wherein the allergen unit is P1 (SEQ ID no 4), the targeting unit is a FGL-2 C-terminal peptide according to SEQ ID no 1.

Further, the fusion protein may comprise a linker. The fusion protein may further comprise a linker to link the first and the second protein together. Said fusion protein may be wherein said linker is RADAAP (SEQ ID no 12) or its nucleotide sequence according to SEQ ID no 46.

Thus, in further embodiments, said fusion protein as described in any embodiment herein is wherein said linker is RADAAP (SEQ ID no 12). Accordingly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, said fusion protein may in still further embodiments be wherein the allergen unit is P5 (SEQ ID no 8), the targeting unit is a FGL-2 C-terminal peptide according to SEQ ID no 1 and the linker is RADAAP (SEQ ID no 12). In still further embodiments, the fusion protein is wherein the allergen unit is P1 (SEQ ID no 4), the targeting unit is a FGL-2 C-terminal peptide according to SEQ ID no 1 and the linker is RADAAP (SEQ ID no 12).

Vaccine Development

It was previously described that cross-linking of the inhibitory receptor FcγRIIb with a B-cell receptor on B-cells leads to anergy and apoptosis of B-cells [20]. On basophils and mast cells that have an IgE receptor (Fcepsilon RI) that binds IgE, cross-linking of the inhibitory receptor with the IgE bound to IgE-receptor could conceivably inhibit the activation of these cells [21].

Since FGL2 is a natural ligand for the inhibitory receptor FcγRIIb the inventors started to test this protein for use in a vaccine against shrimp allergy. The inventors expressed C-terminal fragments of FGL2 in *E. coli* and investigated binding of the fragments to human B-cells by flow cytometry studies. A particular C-terminal fragment of 14.2 kDa (FIG. 1 and FIG. 2) was especially effective in binding to B-cells (FIG. 3) and the inventors therefore focused further on this fragment.

Figure 12:
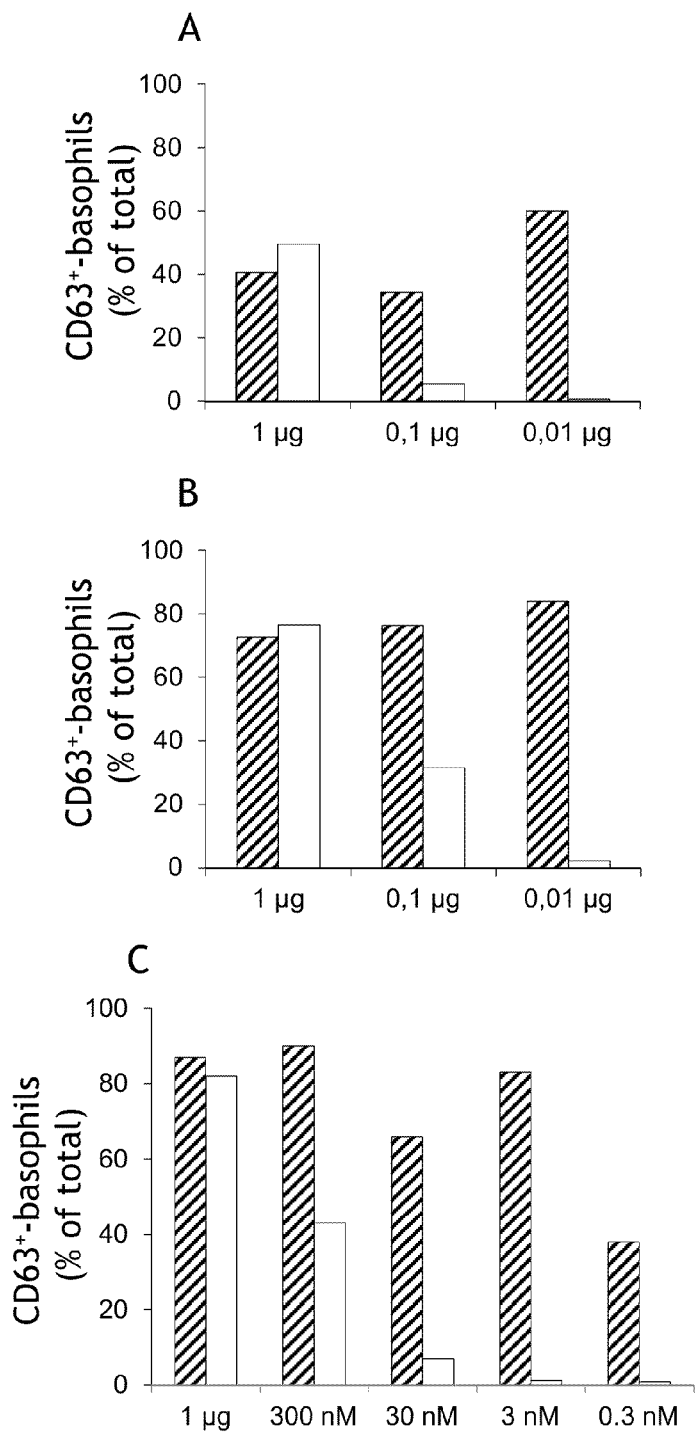

Shrimp tropomyosin is a major allergen in shrimp allergy. Approximately 80% of shrimp allergic individuals respond to this allergen [22], which makes it an excellent model-allergen for development and testing of vaccine-candidates. Therefore, a fusion protein of the above described FGL2 fragment and shrimp tropomyosin was generated by DNA-cloning techniques, expressed in *E. coli*. and tested with several approaches. The fusion protein is abbreviated as FP. Flow cytometry studies using blood samples of healthy and shrimp-allergic individuals showed binding of FP to B-cells (FIG. 11). Basophil-activation tests with the fusion protein showed a strong inhibition of immediate allergic responses by the vaccine compared to the shrimp-allergen alone (expressed in the same expression-system as the vaccine, but lacking the FGL2 ligand) (FIG. 12). Furthermore, skin-prick tests with the vaccine showed a nearly absence of reactivity, while positive responses were observed to similar molar amounts of recombinant allergen (FIG. 13).

In addition, a FP with a truncated allergen was investigated. Recent studies at our laboratory have indicated that some shrimp allergic individuals have a predominant IgE reactivity towards some part of shrimp tropomyosin (unpublished results). Inclusion of a specific allergen domain in the vaccine might therefore increase its efficacy, due to a reduced molar size of the vaccine. An indication for increased activity of the FP with a truncated allergen is increased binding to B-cells of allergic individuals compared to FP (FIG. 11).

Furthermore, the vaccine was tested ex-vivo using a mouse-model for shrimp allergy. In these experiments, mice were sensitized against natural shrimp tropomyosin and B-cell binding and mast cell activation were investigated ex-vivo. The inventors observed that the vaccine bound a large percentage of B-cells (FIG. 18) and induced apoptosis in these cells after ex-vivo incubation (FIG. 19). In line with the human skin prick tests, absence of ex-vivo mast-cell activation was observed against the vaccine, while responses were seen against the recombinant allergen (FIG. 20). In these experiments, the ligand consisted of a homological fragment derived from mouse FGL2.

A Vaccine, its Medical Uses and Methods of Treatment

The fusion protein as provided herein can be used to acutely or chronically inhibit, prevent or treat food allergy, such as shrimp allergy.

A further object of the invention is a fusion protein comprising a first protein and a second protein linked together with a linker, wherein the first protein is an allergen and the second peptide is a targeting unit and the second targeting unit peptide is a FGL-2 C-terminal peptide according to SEQ ID no 1, for medical use. Further, said fusion protein is wherein the allergen unit is shrimp tropomyosin Pan b 1 or parts or fragments thereof (SEQ ID no 15), and the targeting unit is a FGL-2 C-terminal peptide according to SEQ ID no 1.

Particularly, a specific embodiment of said fusion protein is wherein the fusion protein is wherein the allergen unit is P5 (SEQ ID no 8) and the targeting unit is a FGL-2 C-terminal peptide according to SEQ ID no 1. In still another embodiment, the fusion protein is wherein the allergen unit is P1 (SEQ ID no 4) and the targeting unit is a FGL-2 C-terminal peptide according to SEQ ID no 1. There may, of course, be a linker optionally in the fusion protein. Thus, such embodiments are as described in any embodiment herein as exemplified with embodiments wherein said linker is RADAAP (SEQ ID no 12). Accordingly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, said fusion protein may in still further embodiments be wherein the allergen unit is P5 (SEQ ID no 8), the targeting unit is a FGL-2 C-terminal peptide according to SEQ ID no 1 and the linker is RADAAP (SEQ ID no 12). In still further embodiments, the fusion protein is wherein the allergen unit is P1 (SEQ ID no 4), the targeting unit is a FGL-2 C-terminal peptide according to SEQ ID no 1 and the linker is RADAAP (SEQ ID no 12) for medical use.

A further object is use of a fusion protein comprising a first protein and a second protein linked together with a linker, wherein the first protein is an allergen and the second peptide is a targeting unit and the second targeting unit peptide is a FGL-2 C-terminal peptide according to SEQ ID no 1 in the manufacture of a medicament for the treatment and/or prevention of shrimp allergy. Particularly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, specific embodiments of said fusion protein is wherein the allergen unit is P5 (SEQ ID no 8), the targeting unit is a FGL-2 C-terminal peptide according to SEQ ID no 1 and the linker is RADAAP (SEQ ID no 12). In still further embodiments, the fusion protein is wherein the allergen unit is P1 (SEQ ID no 4), the targeting unit is a FGL-2 C-terminal peptide according to SEQ ID no 1 and the linker is RADAAP (SEQ ID no 12) in the manufacture of a medicament for the treatment and/or prevention of shrimp allergy.

Also described herein is a fusion protein comprising a first protein and a second protein linked together with a linker, wherein the first protein is an allergen and the second peptide is a targeting unit and the second targeting unit peptide is a FGL-2 C-terminal peptide according to SEQ IS no 1 for use in the treatment and/or prevention of shrimp allergy. Particularly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, specific embodiments of said fusion protein are wherein the allergen unit is P5 (SEQ ID no 8), the targeting unit is a FGL-2 C-terminal peptide according to SEQ ID no 1 and the linker is RADAAP (SEQ ID no 12) or wherein the allergen unit is P1 (SEQ ID no 4), the targeting unit is a FGL-2 C-terminal peptide according to SEQ ID no 1 and the linker is RADAAP (SEQ ID no 12) for use in the treatment and/or prevention of shrimp allergy.

Further, a fusion protein comprising a first protein and a second protein linked together with a linker, wherein the first protein is an allergen and the second peptide is a targeting unit and the second targeting unit peptide is a FGL-2 C-terminal peptide according to SEQ IS no 1, for use as a vaccine is provided. Particularly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, specific embodiments of said fusion protein are wherein the allergen unit is P5 (SEQ ID no 8), the targeting unit is a FGL-2 C-terminal peptide according to SEQ ID no 1 and the linker is RADAAP (SEQ ID no 12) or wherein the allergen unit is P1 (SEQ ID no 4), the targeting unit is a FGL-2 C-terminal peptide according to SEQ ID no 1 and the linker is RADAAP (SEQ ID no 12), for use as a vaccine is provided.

Further a vaccine composition comprising said fusion protein descried herein comprising a first protein and a second protein linked together with a linker, wherein the first protein is an allergen and the second peptide is a targeting unit and the second targeting unit peptide is a FGL-2 C-terminal peptide according to SEQ ID no 1 and a pharmaceutically acceptable adjuvant or carrier is provided. Particularly, said fusion protein is wherein the allergen unit is shrimp tropomyosin Pan b 1 or parts or fragments thereof (SEQ ID no 15), herein said linker is RADAAP (SEQ ID no 12) and the targeting unit is a FGL-2 C-terminal peptide according to SEQ ID no 1. Further, specific embodiments of said fusion protein are wherein the allergen unit is P5 (SEQ ID no 8), the targeting unit is a FGL-2 C-terminal peptide according to SEQ ID no 1 and the linker is RADAAP (SEQ ID no 12) or wherein the allergen unit is P1 (SEQ ID no 4), the targeting unit is a FGL-2 C-terminal peptide according to SEQ ID no 1 and the linker is RADAAP (SEQ ID no 12) and a pharmaceutically acceptable adjuvant and/or carrier is provided. Pharmaceutically acceptable adjuvants and/or carriers for compositions administered as a vaccine are known in the art and are all useful in the compositions mentioned herein. Particularly, the composition according to the invention be may a liquid composition. Carriers are commonly water, such as buffered water, aqueous humectant, and/or aqueous alcohol mixtures of a consistency appropriate for the selected mode of administration of the composition, e.g., as a paste, gel, tablet, lozenge, syrup, rinse, and so forth. Carriers for liquid vaccine compositions according to the present invention include all known in the art.

As used herein, "pharmaceutical composition" or "pharmaceutical vaccine composition" or simply "vaccine composition" means a therapeutically effective formulation. A "therapeutically effective amount", or "effective amount", or "therapeutically effective", as used herein, refers to that amount which provides a therapeutic effect for a given condition and administration regimen; for example, an amount sufficient to reduce, inhibit or prevent an allergic reaction to a shrimp allergen. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition, e.g. the fusion protein described herein, calculated to produce the desired therapeutic effect in association with the required diluent.

In the methods, uses, kits and for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

It will be appreciated by persons skilled in the art that such an effective amount of the fusion protein or vaccine composition as described herein in all its embodiments and formulation thereof may be delivered as a single bolus dose (i.e. acute administration) or, more preferably, as a series of doses over time (i.e. chronic administration).

For therapeutic use, including prevention, the compounds of the invention can be formulated as pharmaceutical compositions in admixtures with pharmaceutically acceptable carriers or diluents. Methods for making pharmaceutical formulations are well known in the art. It will be appreciated by persons skilled in the art that the fusion protein or vaccine composition will generally be administered in admixture with a suitable pharmaceutical excipient, diluent or carrier selected with regard to the intended route of administration and standard pharmaceutical practice (for example, see Remington: *The Science and Practice of Pharmacy*, 19th edition, 1995, Ed. Alfonso Gennaro, and *Remington's Pharmaceutical Sciences*, 18$^{th}$ Edition, 1990, both from Mack Publishing Company, Pennsylvania, USA, as well as Wang and Hanson "Parenteral Formulations of Proteins and Peptides: Stability and Stabilizers", *Journal of Parenteral Science and Technology, Technical Report No.* 10, Supp. 42-2s (1988). A suitable administration format can best be determined by a medical practitioner for each patient individually, all references which are incorporated herein by reference. Thus, the pharmaceutical composition of the invention comprises the fusion protein as described herein comprising a first peptide and a second peptide linked together with a linker, wherein the first peptide is an allergen and the second peptide is a targeting unit and the second targeting unit peptide is a FGL-2 C-terminal peptide according to SEQ IS no 1, along with conventional carriers, diluents and optionally other ingredients.

Suitable forms of the composition depend upon the user or the route or entry. For example, the fusion protein and vaccine composition can be administered parenteral administration, such as intravenously or intramuscular, intraperitoneal, orally, buccally or sublingually in the form of liquids, tablets, capsules, ovules, elixirs, solutions or suspensions, which may contain flavouring or colouring agents, for immediate-, delayed- or controlled-release applications. The forms of the composition of the fusion protein should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The fusion protein, compositions or pharmaceutical compositions can be administered by different routes including, but not limited to, oral, intravenous, intra-arterial, intraperitoneal, subcutaneous, intranasal or intrapulmonary routes. The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

For systemic administration, injection may be used e.g., intramuscular, intravenous, intra-arterial, etc. For injection, the fusion proteins of the invention are formulated in liquid solutions, such as in physiologically compatible buffers such as Hank's solution or Ringer's solution. Alternatively, the fusion proteins of the invention are formulated in one or more excipients (e.g., propylene glycol) that are generally accepted as safe as defined by e.g. USP standards. They can, for example, be suspended in an inert oil, suitably a vegetable oil such as sesame, peanut, olive oil, or other acceptable carrier. The fusion proteins described herein are suspended in an aqueous carrier, for example, in an isotonic buffer solution at pH of about 5.6 to 9.0. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate acetic acid buffers. A form of repository or "depot" slow release preparation can be used so that therapeutically effective amounts of the preparation are delivered into the bloodstream over many, hours or days following transdermal injection or delivery. In addition, the compounds can be formulated in solid form and re-dissolved or suspended immediately prior to use. Lyophilized forms are also included—see below.

Alternatively, certain fusion proteins in accordance with the present invention can be administered orally. For oral administration, the compounds are formulated into conventional oral dosage forms such as capsules, tablets and tonics. Capsules, tablets and tonics may contain excipients such as microcrystalline cellulose, lactose, sodium citrate, calcium carbonate, dibasic calcium phosphate and glycine, disintegrants such as starch (for example, corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Exemplary excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

The medicaments and agents can also be administered parenterally, for example, intravenously, intra-articularly, intra-arterially, anally intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (for example, to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The fusion protein or vaccine composition can also be administered intranasal or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations may be arranged so that each metered dose or 'puff contains at least 1 mg of a compound of the invention for delivery to the patient. It will be appreciated that the overall daily dose with an aerosol will vary from patient to patient, and may be administered in a single dose or, more usually, in divided doses throughout the day.

Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap. Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor. Devices for controlling particle size of an aerosol are also known, see, for example, U.S. Pat. Nos. 4,790,305; 4,926,852; 4,677,975; and 3,658,059.

For topical administration, the fusion proteins of the invention are formulated into ointments, salves, gels, or creams, as is generally known in the art.

If desired, solutions of the fusion proteins can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween®), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

Further embodiments of a fusion protein or a vaccine composition are in a lyophilized (dry) form. Such lyophilized dry forms may be combined with a dry carrier, for instance, lactose, which is widely used in pharmaceutics. Prior to use, the dry composition or dry pharmaceutical composition will be mixed with appropriate diluent. This may be done in f. ex. a specially designed multi-chamber device, and then immediately after mixing, administered to a mamma in the need thereof, such as a human, for example, in the form of liquid, solution, paste or oral spray.

The amounts of various fusion proteins as described herein for use in the methods of the invention to be administered can be determined by standard procedures. Generally, a therapeutically effective amount is between about 100 mg/kg and 10-12 mg/kg depending on the age and size of the patient, and the disease or disorder associated with the patient. Generally, it is an amount between about 0.05 and 50 mg/kg, or between about 1.0 and mg/kg for the individual to be treated. The determination of the actual dose is well within the skill of an ordinary physician.

The fusion proteins of the present invention may be administered in combination with one or more further therapeutic agents for the treatment of IgE-mediated allergic diseases or conditions. Such further therapeutic agents include, without limitation, corticosteroids, beta-antagonists, theophylline, leukotriene inhibitors, allergen vaccination, and biologic response modifiers such as soluble recombinant human soluble IL-4 receptors (Immunogen), and therapies that target Toll-like receptors. (see, e.g. Barnes, *The New England Journal of Medicine* 341:2006-2008 (1999)). Thus the compounds of the present invention can be used to supplement traditional allergy therapy, such as corticosteroid therapy performed with inhaled or oral corticosteroids.

A further objective is to provide a method for preventing and/or treating shrimp allergy, comprising administering an effective amount of a fusion protein in all its embodiments provided herein comprising a first peptide and a second peptide linked together with a linker, wherein the first peptide is an allergen and the second peptide is a targeting unit and the second targeting unit peptide is a FGL-2 C-terminal peptide according to SEQ ID no 1 or a vaccine composition comprising said fusion protein to a mammal e.g. a human.

Use of a fusion protein in all its embodiments provided herein comprising a first peptide and a second peptide linked together with a linker, wherein the first peptide is an allergen and the second peptide is a targeting unit and the second targeting unit peptide is a FGL-2 C-terminal peptide according to SEQ ID no 1 or a vaccine composition comprising said fusion protein in the vaccination of a mammal, such as a human, for medical use and further, for the treatment and/or prevention of shrimp allergy is also provided.

A Method for Preparing a Fusion Protein

The fusion proteins can be prepared by well-known methods of recombinant DNA technology or traditional chemical synthesis in which the individual polypeptide sequences are directly fused or functionally connected by a polypeptide linker. If the polypeptides are produced by recombinant host cells, cDNA encoding the desired polypeptide of the present invention is inserted into a replicable vector for cloning and expression.

Suitable vectors are prepared using standard techniques of recombinant DNA technology, and are, for example, described in "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4 h edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991). Isolated plasmids and DNA fragments are cleaved, tailored, and ligated together in a specific order to generate the desired vectors. After ligation, the vector containing the gene to be expressed is transformed into a suitable host cell. Host cells can be any eukaryotic or prokaryotic host known for expression of heterologous proteins. Accordingly, the polypeptides of the present invention can be expressed in eukaryotic hosts, such as eukaryotic microbes (yeast) or cells isolated from multicellular organisms (mammalian cell cultures), plants and insect cells. Examples of mammalian cell lines suitable for the expression of heterologous polypeptides include monkey kidney CV1 cell line transformed by SV40 (COS-7, ATCC CRL 1651); human embryonic kidney cell line 293s (Graham et al, J. Gen. Virol. 36:59 [1977]); baby hamster kidney cells (BHK, ATCC CCL 10); Chinese hamster ovary (CHO) cells (Urlaub and Chasin, Proc. Natl. Acad. Sci. USA 77:4216 [1980]; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065), myeloma cells, e.g. SP210, may be used for the production of the fusion molecules herein.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa calfornica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infects the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

*Saccharomyces cerevisiae* is the most commonly used among lower eukaryotic hosts. However, a number of other genera, species, and strains are also available and useful herein, such as *Pichia pastoris* (EP 183,070; Sreekrishna et al., J. Basic Microbiol. 28: 165-278 (1988)). Yeast expression systems are commercially available, and can be purchased, for example, from Invitrogen (San Diego, Calif.). Other yeasts suitable for bi-functional protein expression include, without limitation, *Kluyveromyces* hosts (U.S. Pat. No. 4,943,529), e.g. *Kluyveromyces lactis; Schizosaccharomyces pombe* (Beach and Nurse, Nature 290:140 (1981); *Aspergillus* hosts, e.g. *A. niger* (Kelly and Hynes, EMBO J. 4:475-479

(19851)) and *A. nidulans* (Balance et al., Biochem. Biophys. Res. Commun. 112:284-289 (1983)), and *Hansenula* hosts, e.g. *Hansenula polymorpha*. Yeasts rapidly grow on inexpensive (minimal) media, the recombinant can be easily selected by complementation, expressed proteins can be specifically engineered for cytoplasmic localization or for extracellular export, and they are well suited for large-scale fermentation.

Prokaryotes may be hosts for the initial cloning steps, and are useful for rapid production of large amounts of DNA, for production of single-stranded DNA templates used for site-directed mutagenesis, for screening many mutants simultaneously, and for DNA sequencing of the mutants generated. *E. coli* strains suitable for the production of the peptides of the present invention include, for example, BL21 carrying an inducible T7 RNA polymerase gene (Studier et al., Methods Enzymol. 185:60-98 (1990)); AD494(DE3); EB105; and CB (*E. coli* B) and their derivatives; K12 strain 214 (ATCC 31,446); W3110 (ATCC 27,325); XI776 (ATCC 31,537); HBIOI (ATCC 33,694); JMIOI (ATCC 33,876); NM522 (ATCC 47,000); NM538 (ATCC 35,638); NM539 (ATCC 35,639); etc. Many other species and genera of prokaryotes may be used as well. Indeed, the peptides of the present invention can be readily produced in large amounts by utilizing recombinant protein expression in bacteria, where the peptide is fused to a cleavable ligand used for affinity purification.

Suitable promoters, vectors and other components for expression in various host cells are well known in the art and are disclosed, for example, in the textbooks listed above. Whether a particular cell or cell line is suitable for the production of the polypeptides herein in a functionally active form, can be determined by empirical analysis. For example, an expression construct comprising the coding sequence of the desired molecule may be used to transfect a candidate cell line. The transfected cells are then grown in culture, the medium collected, and assayed for the presence of secreted polypeptide. The product can then be quantitated by methods known in the art, such as by ELISA with an antibody specifically binding a portion of the molecule. In certain instances, especially if the two polypeptide sequences making up the bi-functional fusion protein as described herein are connected with a non-polypeptide linker, it may be advantageous to individually synthesize peptide sequences, e.g. by any of the recombinant approaches discussed above, followed by functionally linking the two sequences.

Alternatively, the two peptide sequences, or the entire molecule, may be prepared by chemical synthesis, such as solid phase peptide synthesis. Such methods are well known to those skilled in the art. In general, these methods employ either solid or solution phase synthesis methods, described in basic textbooks, such as, for example, J. M. Stewart and J. D. Young, *Solid Phase Peptide Synthesis, 2nd* Ed., Pierce Chemical Co., Rockford, Ill. (1984) and G. Barany and R. B. Merrifield, *The Peptide: Analysis Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Thus, a method for preparing a fusion protein as descried herein comprising a first peptide and a second peptide linked together with a linker, wherein the first peptide is an allergen peptide and the second peptide is a targeting unit and wherein the second targeting unit peptide is a FGL-2 C-terminal peptide according to SEQ IS no 1 [CP], comprising the steps of:

a) providing an isolated first allergen peptide from pan b 1 (SEQ ID no 15) or its nucleotide sequence thereof (SEQ ID no 43),
b) providing an isolated second targeting unit peptide or its nucleotide sequence thereof, and wherein the second targeting unit peptide is a FGL-2 C-terminal peptide according to SEQ IS no 1 or its nucleotide sequence according to SEQ ID no 47,
c) optionally providing a linker,
d) fusing the isolated first allergen peptide or its nucleotide sequence thereof in a) above, an isolated second targeting unit peptide or its nucleotide sequence thereof from b), and optionally the linker in c) and wherein the second targeting unit peptide is a FGL-2 C-terminal peptide according to SEQ ID no 1 in b) above, and
e) optionally isolation of said fusion protein.

Further embodiments of the method are wherein said isolated first allergen peptide from pan b 1 is any of the peptides P1 (SEQ ID no 4), P2 (SEQ ID no 5), P3 (SEQ ID no 6), P4 (SEQ ID no 7) or P5 (SEQ ID no 8). Still even further embodiments of the methods are wherein the linker is RADAAP (SEQ ID no 12) or its nucleotide sequence according to SEQ ID no 46. Still even further embodiments are wherein said fusion protein is isolated. Suitable means for isolation herein are given and one example is a Histag according to its sequence provided in SEQ ID no 9 or its nucleotide sequence provided in SEQ ID no 45. Said Histag is usable for all embodiments of the fusion protein or peptides provided herein as exemplified e.g in the examples. Thus, in further embodiments, said method is a method to prepare fusion proteins wherein the allergen unit is P5 (SEQ ID no 8), the targeting unit is a FGL-2 C-terminal peptide according to SEQ ID no 1 and the linker is RADAAP (SEQ ID no 12) or a fusion protein is wherein the allergen unit is P1 (SEQ ID no 4), the targeting unit is a FGL-2 C-terminal peptide according to SEQ ID no 1 and the linker is RADAAP (SEQ ID no 12).

A Kit

A kit of parts comprising a fusion protein comprising a first peptide and a second peptide optionally linked together with a linker, wherein the first peptide is an allergen and the second peptide is a targeting unit and the second targeting unit peptide is a FGL-2 C-terminal peptide according to SEQ IS no 1 or a vaccine composition comprising said fusion protein, a container comprising said fusion protein or vaccine composition and optionally instructions for its use id further provided herein. In specific embodiments, said kit comprises a fusion protein wherein the allergen unit is peptide from pan b 1 (SEQ ID no 15), the targeting unit is a FGL-2 C-terminal peptide according to SEQ ID no 1 and the linker is RADAAP (SEQ ID no 12), a fusion protein wherein the allergen unit is P5 (SEQ ID no 8), the targeting unit is a FGL-2 C-terminal peptide according to SEQ ID no 1 and the linker is RADAAP (SEQ ID no 12) or a fusion protein is wherein the allergen unit is P1 (SEQ ID no 4), the targeting unit is a FGL-2 C-terminal peptide according to SEQ ID no 1 and the linker is RADAAP (SEQ ID no 12). Said kit may further comprise a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The container may also be an inhalation device such as those discussed above. At least one active agent in the composition is a fusion protein of the invention. The label or package insert indicates that the composition comprising the fusion proteins herein is used for treating the condition of choice, such as an allergic condition, e.g. shrimp allergy as discussed above. The kit may further comprise a further container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further, said kits may include suitable control samples (i.e. reference samples), and/or positive or negative control samples.

In some embodiments, a kit may further include instructional materials disclosing, for example, means for use of a fusion protein comprising a first peptide and a second peptide linked together with a linker, wherein the first peptide is an allergen and the second peptide is a targeting unit and the second targeting unit peptide is a FGL-2 C-terminal peptide according to SEQ ID no 1 or a vaccine composition comprising said fusion protein or means of use for a particular reagent. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

The kit may further comprise, in an amount sufficient for at least use, preferably several uses, a fusion protein comprising a first peptide and a second peptide linked together with a linker, wherein the first peptide is an allergen and the second peptide is a targeting unit and the second targeting unit peptide is a FGL-2 C-terminal peptide according to SEQ ID no 1 or a vaccine composition comprising said fusion protein as a separately packaged reagent.

Instructions for use of the packaged reagent are also typically included. Such instructions typically include a tangible expression describing reagent concentrations or the relative amounts of reagent and sample to be mixed, maintenance time periods for reagent/sample admixtures, temperature, buffer conditions and the like.

Certain kit embodiments can include a carrier means, such as a box, a bag, a satchel, plastic carton (such as moulded plastic or other clear packaging), wrapper (such as, a sealed or sealable plastic, paper, or metallic wrapper), or other container.

In some examples, kit components will be enclosed in a single packaging unit, such as a box or other container, which packaging unit may have compartments into which one or more components of the kit can be placed. In other examples, a kit includes a one or more containers, for instance, vials, tubes, and the like that can retain.

Other kit embodiments include, for instance, syringes, cotton swabs, or latex gloves, which may be useful for handling, collecting and/or processing a biological sample. Kits may also optionally contain droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

All patent and non-patent references cited in the present application, are hereby incorporated by reference in their entirety.

As used herein, the singular forms "a", "and", and "the" include plural referents unless the context clearly dictates otherwise.

As used herein "at least one" is intended to mean one or more, i.e. 1, 2, 3, 4, 5, 6, 7, 8, 9, 10, etc.

Non-limiting examples which embody certain aspects of the invention will now be described.

REFERENCE LIST

1. Sampson H A. Update on food allergy. Journal of Allergy and Clinical Immunology 2004; 113:805-19.
2. Sicherer S H. Food allergy. The Lancet 2002; 360:701-10.
3. Foucard T, Malmheden Yman I. A study on severe food reactions in Sweden—is soy protein an underestimated cause of food anaphylaxis? Allergy 1999; 54:261-5.
4. Patel D A, Holdford D A, Edwards E, Carroll N V. Estimating the economic burden of food-induced allergic reactions and anaphylaxis in the United States. Journal of Allergy and Clinical Immunology 2011; 128:110-5.e5.
5. Sicherer S H, Munoz-Furlong A, Sampson H A. Prevalence of seafood allergy in the United States determined by a random telephone survey. The Journal of allergy and clinical immunology 2004; 114:159-65.
6. Ben-Shoshan M, Harrington D W, Soller L, Fragapane J, Joseph L, St Pierre Y, Godefroy S B, Elliott S J, Clarke A E. A population-based study on peanut, tree nut, fish, shellfish, and sesame allergy prevalence in Canada. The Journal of allergy and clinical immunology 2010; 125:1327-35.
7. Cappella A, Durham S R. Allergen immunotherapy for allergic respiratory diseases. Human vaccines & immunotherapeutics 2012; 8.
8. Kündig T M. Immunotherapy concepts under investigation. Allergy 2011; 66:60-2.
9. Lieberman J, Chehade M. Use of Omalizumab in the Treatment of Food Allergy and Anaphylaxis. Current Allergy and Asthma Reports: 1-7.
10. Koyama T, Hall L R, Haser W G, Tonegawa S, Saito H. Structure of a cytotoxic T-lymphocyte-specific gene shows a strong homology to fibrinogen beta and gamma chains. Proceedings of the National Academy of Sciences 1987; 84:1609-13.
11. Chan C W, Chan M W, Liu M, Fung L, Cole E H, Leibowitz J L, Marsden P A, Clark D A, Levy G A. Kinetic analysis of a unique direct prothrombinase, fgl2, and identification of a serine residue critical for the prothrombinase activity. Journal of immunology (Baltimore, Md.: 1950) 2002; 168:5170-7.
12. Yuwaraj S, Ding J, Liu M, Marsden P A, Levy G A. Genomic Characterization, Localization, and Functional Expression of FGL2, the Human Gene Encoding Fibroleukin: A Novel Human Procoagulant. Genomics 2001; 71:330-8.
13. Chan C W Y, Kay L S, Khadaroo R G, Chan M W C, Lakatoo S, Young K J, Zhang L, Gorczynski R M, Cattral M, Rotstein O, Levy G A. Soluble Fibrinogen-Like Protein 2/Fibroleukin Exhibits Immunosuppressive Properties: Suppressing T Cell Proliferation and Inhibiting Maturation of Bone Marrow-Derived Dendritic Cells. The Journal of Immunology 2003; 170:4036-44.
14. Xie L, Ichimaru N, Morita M, Chen J, Zhu P, Wang J, Urbanellis P, Shalev I, Nagao S, Sugioka A, Zhong L, Nonomura N, Takahara S, Levy G A, Li X-K. Identification of a novel biomarker gene set with sensitivity and specificity for distinguishing between allograft rejection and tolerance. Liver Transplantation 2012; 18:444-54.

15. Turner H, Kinet J P. Signalling through the high-affinity IgE receptor Fc epsilonRI. Nature 1999; 402:B24-30.
16. Cassard L, Jönsson F, Arnaud S, Daëron M. Fcγ Receptors Inhibit Mouse and Human Basophil Activation. The Journal of Immunology 2012; 189:2995-3006.
17. Daeron M, Malbec O, Latour S, Espinosa E, Pina P, Fridman W H. Regulation of tyrosine-containing activation motif-dependent cell signalling by Fc gamma RII. Immunol Lett 1995; 44:119-23.
18. Cemerski S, Chu S Y, Moore G L, Muchhal U S, Desjarlais J R, Szymkowski D E. Suppression of mast cell degranulation through a dual-targeting tandem IgE-IgG Fc domain biologic engineered to bind with high affinity to FcγRIIb. Immunology Letters 2012; 143:34-43.
19. Horton H M, Chu S Y, Ortiz E C, Pong E, Cemerski S, Leung I W L, Jacob N, Zalevsky J, Desjarlais J R, Stohl W, Szymkowski D E. Antibody-Mediated Coengagement of FcγRIIb and B Cell Receptor Complex Suppresses Humoral Immunity in Systemic Lupus Erythematosus. The Journal of Immunology 2011; 186:4223-33.
20. Lehmann B, Schwab I, Böhm S, Lux A, Biburger M, Nimmerjahn F. FcγRIIB: a modulator of cell activation and humoral tolerance. Expert Review of Clinical Immunology 2012; 8:243-54.
21. Chu S Y, Horton H M, Pong E, Leung I W L, Chen H, Nguyen D-H, Bautista C, Muchhal U S, Bernett M J, Moore G L, Szymkowski D E, Desjarlais J R. Reduction of total IgE by targeted coengagement of IgE B-cell receptor and FcγRIIb with Fc-engineered antibody. Journal of Allergy and Clinical Immunology 2012; 129:1102-15.
22. Gamez C, Sanchez-Garcia S, Ibanez M D, Lopez R, Aguado E, Lopez E, Sastre B, Sastre J, del Pozo V. Tropomyosin IgE-positive results are a good predictor of shrimp allergy. Allergy 2011; 66:1375-83.
23. Le Gall F, Reusch U, Little M, Kipriyanov S M. Effect of linker sequences between the antibody variable domains on the formation, stability and biological activity of a bispecific tandem diabody. Protein engineering, design & selection: PEDS 2004; 17:357-66.
24. Tedder T F, Engel P. CD20: a regulator of cell-cycle progression of B lymphocytes. Immunology Today 1994; 15:450-4.
25. Jensen B M, Swindle E J, Iwaki S, Gilfillan A M. Generation, Isolation, and Maintenance of Rodent Mast Cells and Mast Cell Lines Current Protocols in Immunology: John Wiley & Sons, Inc., 2001.
26. Larson D, Mitre E. Histamine release and surface CD200R1 staining as sensitive methods for assessing murine mast cell activation. Journal of Immunological Methods 2012; 379:15-22.
27. Myrset H R, Barletta B, Di Felice G, Egaas E, Dooper M M B W. Structural and Immunological Characterization of Recombinant Pan b 1, a Major Allergen of Northern Shrimp, Pandalus borealis. International Archives of Allergy and Immunology 2013; 160:221-32.
28. Ayuso R, Lehrer S B, Reese G. Identification of Continuous, Allergenic Regions of the Major Shrimp Allergen Pen a 1 (Tropomyosin). International Archives of Allergy and Immunology 2002; 127:27-37.
29. Vinje N E, Larsen S, Løvik M. A mouse model of lupin allergy. Clinical & Experimental Allergy 2009; 39:1255-66.
30. Capobianco F, Butteroni C, Barletta B, Corinti S, Afferni C, Tinghino R, Boirivant M, Di Felice G. Oral sensitization with shrimp tropomyosin induces in mice allergen-specific IgE, T cell response and systemic anaphylactic reactions. International Immunology 2008; 20:1077-86.

EXAMPLES

Materials and Methods for all Examples (if not Indicated Otherwise)

Cloning cDNA clones of human and mouse FGL2 were obtained from Invitrogen (5219649, accession BC033820 and 4189071, accession BC028893, respectively). The C-terminal part of the human and mouse FGL2 proteins were cloned and are hereafter called CP (human) or mCP (mouse). The proteins were amplified by PCR and cloned into the vector pET19b (Novagen, Darmstadt, Germany) by In-Fusion cloning (Clonetech, Saint-Germain-en-Laye, France) with 15 overlapping base pairs from the vector according to the instructions from the manufacturer (underlined).

```
The forward primers (fp) were:
Human FGL2_CP_fp:
                                       (SEQ ID no 28)
5'-gacgacgacgacaagggagatgcattacgt -3'

Mouse FGL2_mCP_fp:
                                       (SEQ ID no 30)
5'-gacgacgacgacaaggggatgccttgcgt-3'

The reverse primers (rp) were:
Human FGL2_CP_rp:
                                       (SEQ ID no 29)
5'-gctttgttagcagcccagagtgatttatggcttaaagtgcttggg-
3'

Mouse FGL2_mCP_rp:
                                       (SEQ ID no 31)
5'-gctttgttagcagcccagagtgatttatggcttgaaattcttggg-
3'
```

Primers used for cloning of the cDNA for the fusion protein (FP) consisting of shrimp tropomyosin, a short linker (RADAAP (SEQ ID no 12), adopted from Le Gall et al. [23]) and CP were:

```
Tropomyosin_fp:
                                       (SEQ ID no 32)
5' gacgacgacgacaagatggacgccatcaagaagaag 3'

Tropomyosin_rp:
                                       (SEQ ID no 33)
5' tggtgcagcatcagccggtagccagacagttcgctga 3'

FGL2-peptide_fp:
                                       (SEQ ID no 34)
5' cgggctgatgctgcaccaggagatgcattacgt 3'

(SEQ ID no 29)
The reverse primer was FGL2_rp as
described above.
```

Primers used for cloning of the cDNA for the fusion protein consisting of shrimp tropomyosin, a short linker (RADAAP (SEQ ID no 12), and mCP were: Tropomyosin fp and rp was as described above for FP.

```
mCP_mFP_fp:
                                       (SEQ ID no 41)
5'-cgggctgatgctgcaccaggggatgccttgcgt-3'
```

The reverse primers mCP in mFP were similar to FGL2_mCP_rp as described above (SEQ ID no 31).

The nucleotides coding for the linker RADAAP (SEQ ID no 46) are written in bold text. The overlapping base pairs used for in-fusion cloning are underlined. The primers were synthesized at Eurofins MWG (Ebersberg, Germany).

Primers for cloning of a fusion protein with tropomyosin P1 and CP were:

```
P1 for fusion protein_fp:
                                    (SEQ ID no 18)
5' gacgacgacgacaagatggacgccatcaagaagaagatg 3'.

Peptide 1 for fusion protein_rp
                                    (SEQ ID no 36)
5' tggtgcagcatcagcccggagagccttgtccttctcctc 3'
```

Primers for CP are similar to the primers for CP written above for FP with whole tropomyosin.

Primers for cloning of a fusion protein with tropomyosin P5 and CP were:

```
P5 for fusion protein_fp:
                                    (SEQ ID 37)
5' gacgacgacgacaagaagactctcaccaacaagctgaag 3'

P5 for fusion protein_rp,
similar to whole tropomyosin rp in FP:
                                    (SEQ ID 38)
5'-gctttgttagcagccttagtagccagacagttcgctga-3'
```

Primers for CP are similar to the primers for CP written above for FP with whole tropomyosin.

The constructs were expanded in XL10-Gold cells (Stratagene, San Diego, USA), plasmid DNA was isolated by QIAprep Spin Miniprep Kit (Qiagen) and the inserts were sequenced by GATC-biotech. The pET19b vectors encoding the proteins linked to an N-terminal decahistidine tag and an enterokinase cleavage site (MG<u>HHHHHHHHHH</u>SSGHI <u>DDDDK</u>, SEQIDno9) were then transformed into *E. coli* Rosetta™ 2(DE3) competent cells (Novagen) for expression.

Expression and Purification of Proteins

Expression of the proteins was performed using the Overnight Express™Autoinduction System 1 (Novagen). Cells were harvested by centrifugation (20 min, 5500×g, 4° C.) and frozen at −80° C. Protein was extracted using 5 mL/g pellet of a denaturing extraction buffer (50 mM $NaH_2PO_4$, 300 mM NaCl, 10 mM imidazole, 8 M urea, pH 7.4). The proteins were purified by immobilized metal affinity chromatography (IMAC) using HisPur Cobalt Spin Columns according to the manufactures instructions (Pierce Biotechnology, Rockford, USA). CP and mCP were dialysed against PBS de Boer (4.4 mM $Na_2HPO_4×2H_2O$, 2.5 mM $NaH2PO4×H_2O$, 145 mM NaCl, pH: 9.0). The fusion proteins FP and mFP were purified further by size-exclusion chromatography (SEC, Superdex pg (16/60), GE Healthcare, Buckinghamshire, UK) with phosphate buffer (50 mM $NaPO_4$, 150 mM NaCl, pH 9.0) as a mobile phase. Recombinant tropomyosin (rT) was purified by size-exclusion chromatography (SEC, Superdex 75 pg (16/60), GE Healthcare) with MOPS (20 mM, 500 mM NaCl, pH 7.4) as a mobile phase. Protein concentrations were determined by the Lowry method (DC protein assay, Bio-Rad, Hercules, USA) using bovine serum albumin as a standard.

Natural Tropomyosin Pan b 1

Natural Pan b 1 was obtained from frozen, peeled, boiled *P. borealis* caught in the Oslofjord (Norway). The protein was extracted as previously described [22], followed by SEC purification as described for rPan b 1. The protein concentration was determined by the Lowry method.

Study Subjects

Six individuals with positive skin prick tests (SPT) to shrimp extract (*P. borealis*, ALK-Abelló A/S, Hoersholm, Denmark) were recruited at Haukeland University Hospital (Bergen, Norway). Clinical and laboratory features of the shrimp-allergic individuals are listed in FIG. 21. Approval of the studies involving human subjects was obtained from the Norwegian National Ethical Board.

SDS-PAGE and Immunoblotting

Proteins were separated by SDS-PAGE under reducing conditions using 4-12% Bis-Tris pre-cast gels (Invitrogen) and detected by SimplyBlue SafeStain (Invitrogen). For immunoblot analysis, proteins were electrophoretically transferred from the gels to nitrocellulose membranes (pore size 0.45 µm, Bio-Rad). Membranes were blocked with PBS containing 0.05% Tween-20 (PBST) and 3% horse serum for 1 h, following incubation with patient serum (diluted 1:30) overnight at 4° C. in blocking buffer. For IgE detection, membranes were first incubated with rabbit anti-human IgE (1:6000, DakoCytomation, Glostrup, Denmark) and then with goat anti-rabbit IgG horseradish peroxidase conjugate (1:5000, Zymed, San Francisco, USA), each for 1 h. IgE binding was revealed with 3,3'5,5' tetramethylbenzidine (TMB) substrate (Single solution, Zymed). Between the different incubation steps, blots were washed three times with PBST for 15 min. All incubation and washing steps were performed at room temperature with gentle shaking. Novex® Sharp Pre-Stained Protein Standard (Invitrogen) was used as protein size marker.

Human B-Cell Studies

CD20 is a transmembrane protein found primarily on B-cells [24]. Measurement of binding of His-tagged protein to B-cells was done by flow cytometry. Fresh blood was collected in ml tubes each containing 7.2 mg $K_2EDTA$ (Vacutainer®, BD, Franklin Lakes, USA). Whole blood aliquots (50 µL) were diluted 1:1 with a solution containing FITC labelled anti-CD20 (1 µg, Santa Cruz Biotechnology, Santa Cruz, USA), his-tagged protein solution (11 µl) and wash buffer (34 µl, Bühlmann Laboratories, Allschwil, Switzerland). Cells were incubated at RT for 30 minutes under gentle shaking. Erythrocytes were lysed by addition of 3 ml of a lysis solution (1.5 M $NH_2Cl$, 100 mM $KHCO_3$, 1 mM EDTA, pH 7.2) and incubation for 8 min at RT. Cells were washed and bound proteins were stained with a Alexa fluor647 labelled anti-His antibody (1:100, Qiagen) at 4° C. in the dark for 30 minutes. After two washings cells were resuspended in wash solution and analysed with a flow cytometer (Accuri C6). Single cells were selected by gating and a minimum of 10 000 cells was analysed.

ELISA

CP, FP, FP1, FP5 and control protein human albumin (Sigma Aldrich) were coated at 10, 5 and 2.5 µg/mL in 0.05 M carbonate-bicarbonate buffer, pH 9.6, (Sigma-Aldrich) on high binding flat bottomed, 96-well microplates (Corning Inc., Corning, USA) at 37° C. for 1 h (100 µL/well). Plates were blocked with 2.5% w/v bovine serum albumin in PBS (200 µL/well). Plates were washed and incubated with recombinant 1 µg/ml human FcγRIIb (Sino Biological) in PBS containing 0.05% Tween-20 (PBST) for 1 h at room temperature with gentle shaking. For detection of bound FcγRIIb, wells were first incubated with anti-FcγRIIb antibody (Sino Biological) and thereafter incubated with rabbit anti-mouse-HRP (Dako Cytomation). Binding was finally revealed with K-Blue TMB substrate solution (75 µL/well, Neogen, Lexington, USA). The reaction was stopped with 2 M H2SO4 (50 µL/well) and optical density was read at 450 nm. In between all steps, plates were washed at least three times with PBST.

Basophile Activation Test (BAT)

The FIow2CAST was performed according to the manufacturer's instructions (Bühlmann Laboratories) and has been fully described elsewhere [24]. Flow cytometric analysis was performed using an Accuri C6 flow cytometer (Accuri Cytometers Ltd., Cambs, UK) with CFlow Plus software. In each assay, at least 500 basophils were assessed. The up-regulation of the activation marker CD63 was calculated by the percentage of the CD63-positive cells compared to the total number of identified basophilic cells.

Skin Prick Test (SPT)

SPTs were performed with natural tropomyosin (SEQ ID 15), recombinant tropomyosin (rT, SEQ ID No 3), with solutions of 15 and 4.0 µM) and fusion protein FP (4.0 µM). Histamine hydrochloride (10 mg/mL, ALK—Abelló A/S) and phosphate buffer (50 mM $NaPO_4$, 150 mM NaCl, pH 9.0) were used as positive and negative controls respectively. Twenty microliter aliquots of the test solutions were placed on the patients' forearms and pricked in double with a minimum of 3 cm distance between individual application points. Reactions were recorded after 15 min. A positive SPT result to an allergen was defined by a mean duplicate reaction diameter equal to or larger than 3 mm greater than that of the negative control.

Mouse Studies

Animals. Female inbred C3H/HeJ mice (Jackson Laboratories, Bar Harbor, Me., USA), 5 weeks old at the start of the experiments, were used. The animals were housed, 6 mice per cage, on NESTPAK bedding (Datesand Ltd, Manchester, UK) in type III macrolon cages in filter cabinets (Scantainers), exposed to a 12-hr/12-hr light/dark cycle (30-60 lux in cages), room temperature of 21±2° C. and 35-75% humidity. Pelleted food (RM1; SDS, Essex, UK) and tap water ad libitum were given. Before entering the experiments, the animals were allowed to rest for 1 week. The experiments were performed in conformity with the laws and regulations for experiments with live animals in Norway and were approved by the Norwegian Animal Research Authority under the Ministry of Agriculture.

Mice were immunized by peroral administration of 100 µg of purified shrimp tropomyosin (nT) per mouse together with 10 µg per mouse of cholera toxin (*Vibrio cholerae*, azide free; EMD Biosciences Inc., CA, USA) as an adjuvant in a total of 200 µl of an isotonic bicarbonate solution (B-saline, eight parts of HBSS and two parts of 7.5% sodium bicarbonate), to neutralize stomach acidity, on days 0, 1, 2, 7, 21, 28, 35 and 42. Control animals received equal amounts of CT alone (10 µg per mouse). On days 0, 12, 28 and Blood samples were obtained from v. saphena [25, 26] to monitor serum IgE levels. Mice were anaesthetized using hypnorm/dormicol anaesthesia, exsanguinated and cervical dislocation was performed.

Mouse B-Cell Studies

Spleen cells were prepared by pressing the spleens through a 70-µm cell strainer (BD Labware, Franklin Lakes, N.J., USA) using Dulbecco's modified eagles medium (DMEM with 2% foetal calf serum FCS). Cell suspensions were centrifuged and erythrocytes were lysed as described above for human B-cells. Cells were washed twice and cell concentrations were determined using a Bürker-Türk cell counter. Incubations were performed in culture medium (DMEM, supplemented with 10% FCS and 1% streptomycin/penicillin) with or without allergen (natural and recombinant shrimp tropomyosin), mCP, mFP, recombinant mouse FGL2 (R&D Systems) at cell concentrations of 500 000 cells/well, at 37° C. and 5% CO2 for 4 hours. Afterwards, cells were washed and stained with anti-CD19 (B-cell marker, Southern Biotech, Birmingham, USA) and Alexa fluor647 labelled anti-His antibody (1:100, Qiagen) at 4° C. in the dark for minutes. After two washings cells analysed with a flow cytometer (Accuri C6). Single cells were selected by gating and a minimum of 10 000 cells was analysed. In parallel, cells were incubated with anti-CD19 and FITC-conjugated recombinant Annexin V (ImmunoTools, Friesøythe, Germany) according to the guidelines of the manufacturer for the determination of apoptotic B-cells.

Peritoneal mast cells were purified as previously described [25, 26]. In short, peritoneal cells were obtained by lavage and erythrocytes were lysed as described above. Mast cells were isolated by a 70% Percoll gradient and incubated at a concentration of 750 000 cells per well in DMEM containing 10% FCS, 2 mM L-glutamine, 50 µg/ml gentamicin and 20 mM HEPES), pH 7.4, and allergens or control proteins at indicated concentrations. Activation of mast cells was investigated by CD200R1 upregulation as previously described [26] using rat anti-mouse CD200R1 (AbD Serotek).

Example 1

Figure 2:
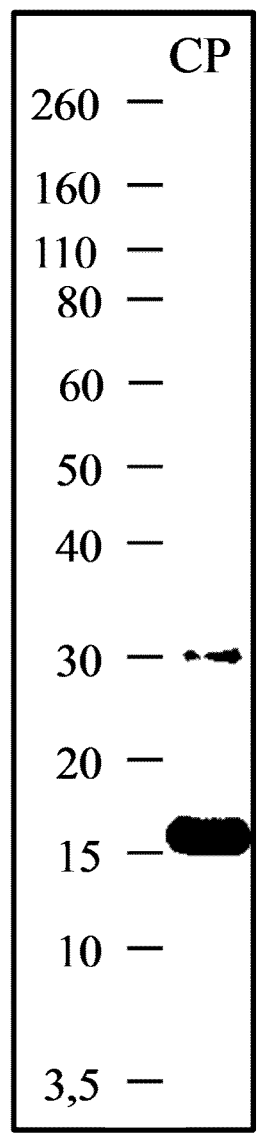

Generation and Characterization of FP; a Fusion Protein Consisting of Shrimp Tropomyosin, a Linker and a C-Terminal FGL2 Peptide CP Design and identification of CP. A C-terminal FGL2 peptide was designed with a FGL2 sequence length of 101 amino acids in order to prevent any possible prothrombinase activity (FIG. 1A). The protein was generated using a *E. coli* expression system and was purified by IMAC, as described in the methods part. Peptide mass fingerprint analysis of CP provided amino acid recognition of 79% (FIG. 1B). The calculated mass of CP 14.2 kDa. In SDS-PAGE analysis of eluate 1, 2 and 3 after IMAC purification, CP appeared as bands with the approximate weights of 17 kDa (FIG. 2).

Figure 3:
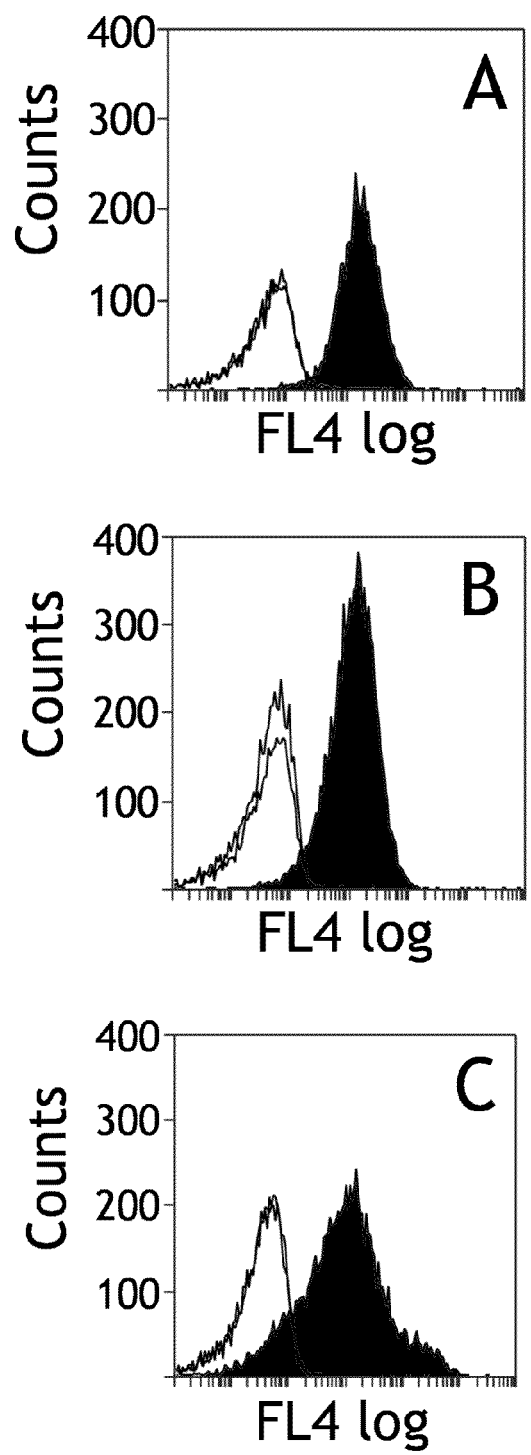

The binding of CP to B-cells was investigated using flow cytometry analysis. FIG. 3 shows that histidin-tagged CP bound on B-cells of normal, non-atopic individuals, while little binding was seen to other cells (data not shown).

Since CP showed a strong binding to B-cells, this peptide was fused to shrimp tropomyosin by DNA cloning techniques (FIG. 4a). A short linker consisting of the amino acids RADAAP were used as a linker. This linker was previously shown to be easily expressed in *E. coli* expression system [23], which would be favourable for the FP. In order to maximize binding of CP, the histidin-tag and tropomyosin were fused N-terminally and hereafter this protein is called FP. FP was expressed in *E. coli* and had the theoretical weight of 47.6 kDa. After SDS-PAGE proteins appeared as a protein with a molecular weight of approximately 52 kDa (FIG. 5). FP is probably in a dimeric or multimeric state, since an additional band was observed at the height of 100 kDa. An illustration of the proposed structure was given (FIG. 6).

Since FGL2 has previously been shown to bind to FcγRIIb, we performed an experiment in which we tested binding of the receptor to immobilized CP and FP. We observed binding at coating concentrations of 10, 5 and 2.5 µg/mL, which indicates ligand-receptor interaction. It is therefore likely that CP binds to B-cells via FcγRIIb.

In the next experiment it was tested to what extent CP and the fusion proteins bound to the surface of B-cells of shrimp allergic individuals. The characteristics of the allergic individuals involved in this study are described in FIG. 21. Using flow cytometry, we observed that CP bound to approximately 40% of B-cells of shrimp allergic individuals (mean of 4 patients). As expected, recombinant tropomyosin bound to a low number of B-cells, not significantly different from the control protein (recombinant his-tagged CD16). The fusion protein FP bound on average to approximately 3.4% of the B-cells, which was significantly different from rT and control incubations (Two sided Student's t-test).

It was then investigated whether FP would induce a lower number of basophils than the allergen alone (without CP attached). We therefore performed basophil activation tests (as described in the methods part) with recombinant tropomyosin and FP and measured activation of basophils. It was observed that CP induced a comparable activation of basophils at 1 µg/ml, but much lower activation of basophils at lower concentrations. These results indicate that CP lowers the sensibility of the basophils for the allergen. These results are in line with previous studies describing that cross-linking of FcγRIIb with FcεRI inhibits activation of basophils [16].

We then investigated the effect of the FP in an in vivo setting, by skin prick testing of five shrimp allergic individuals. In skin-prick tests, the reactivity local mast cells towards allergen in the skin are investigated. In line with previous studies [27], we observed that recombinant and natural tropomyosin induced activation of skin mast cells (wheal sizes above 3 mm (see methods text for calculations) at an allergen concentration of 15 µM. At lower concentrations (4 µM) recombinant allergen induced positive responses in three of five individuals. In contrast, a similar molar amount of FP, and thus containing a similar amount of tropomyosin molecules, induced no positive responses (FIG. 13). Overall, in line with the previous results in basophil activation test, these results indicate that the presence of CP inhibits allergic responses towards the allergen tropomyosin.

Example 2

Generation and Characterization of a Fusion Protein Consisting of a Fragment of Shrimp Tropomyosin and a C-Terminal FGL2 Peptide CP Since shrimp tropomyosin has a coiled-coil alpha-helix structure with 5 important IgE binding domains [28], we wanted to investigate whether inclusion of a single IgE binding domain could be of advantage of the structure of the FP. We therefore cloned and expressed five parts of tropomyosin (FIG. 7) and included two of those (region 1 and 5) in a fusion protein with CP. These constructs are hereafter called FP1 and FP5 and thus consist of an N-terminal histidin-tag, the tropomyosin fragment, the short linker, RADAAP (SEQ ID no 12) and CP (FIG. 8). The proteins were expressed in *E. coli* expression system and results indicated that these proteins also have a dimeric structure (SDS-PAGE, FIG. 9). The shortened fusion proteins were also tested in receptor binding studies (ELISA) and were found to have comparable receptor binding activity as CP and FP (FIG. 10). In addition, FP5 was tested in a B-cell binding assay, and appeared to bind to a higher amount of B-cells of shrimp allergic individuals than FP, but lower than CP.

Overall, these results indicate that a fusion protein containing a fragment of shrimp tropomyosin has the correct structure. In previous studies in which sensitization towards the five shrimp fragments was investigated, it was found that some individuals have most reactivity to fragments 1 and 5. In theory, a FP1 and FP5 could be a possible 'tailor made' treatment for these patients.

Example 3

Generation of a Murine Fusion Protein Consisting of Shrimp Tropomyosin and a C-Terminal Mouse FGL2 Peptide mCP A murine homologue of human CP (mCP, FIG. 14) was cloned and expressed in *E. coli* (FIG. 15). CP was included to generate a murine version of FP, and was designated mFP. mFP consisted a N-terminal histidin-tag, shrimp tropomyosin, a short linker and mCP (FIG. 16). SDS-PAGE analysis showed a protein of approximately 50 kDa in size, and presence of proteins of approximately 100 kDa in size, which indicates dimerization of the fusion protein.

In order to test whether mFP was capable of binding murine B-cells and inhibit allergic responses, an animal experiment was performed. Female inbred C3H/HeJ mice were immunized per-orally with shrimp tropomyosin (Pan b 1) in presence of cholera toxin. This protocol results in tropomyosin sensitized mice with specific serum IgE over time and show anaphylactic reactions after challenge with the specific allergen [29, 30].

In this study we included 6 mice in the experimental group receiving tropomyosin plus cholera toxin, and 6 control mice that received cholera toxin only. At the end of the study, blood was drawn, peritoneal mast cells were collected and purified and spleens were collected for B-cell binding studies. Ex-vivo incubation with natural shrimp tropomyosin, recombinant tropomyosin, mCP, mFP, without antigen, and with recombinant mouse FGL2 were performed. Results show that mFP binds to more than 90% of the B-cells (FIG. 18). mFP bound a much higher number of B-cells than mCP or recombinant FGL2. A positive control was also included in this study, anti-FcγRIIb, and showed binding to approximately 70% of the B-cells (FIG. 18).

We wanted to investigate whether binding of mFP would result in induction of apoptosis in these B-cells. Experiments were performed in parallel to the B-cell binding studies described above and included incubation with annexin-V as a marker for apoptosis induction. It appeared that mFP induced the highest percentage of apoptotic B-cells (approximately 15%) compared to the other proteins tested (nT, rT, mCP and recombinant FGL2) that induced much lower numbers of apoptotic B-cells (FIG. 19). Subsequently we investigated the activation of peritoneal mast cells by mFP in comparison to allergen alone (without CP). CD200R1 was used as a cell surface marker for mast cell activation (see methods). In this experiment, a percentage above 5% positive mast cells is regarded as a positive reaction to the allergen. A positive reaction was observed against nT and rT, but not mFP and mCP (FIG. 20). This therefore indicates that the presence of CP inhibits the allergen specific activation of mast cells.

What is claimed is:

1. A fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2.

2. The fusion protein according to claim 1, wherein the allergen is shrimp tropomyosin Pan b 1 (SEQ ID No: 15) parts or fragments thereof.

3. The fusion protein according to claim 2, wherein the fragments of shrimp tropomyosin Pan b1 comprises the sequence according to any one of SEQ ID Nos: 4, 5, 6, 7, or 8.

4. The fusion protein according to claim 1, wherein the allergen is shrimp tropomyosin peptide 5 (P5) (SEQ ID No: 8).

5. The fusion protein according to claim 1, wherein the allergen is shrimp tropomyosin peptide 1 (P1) (SEQ ID No: 4).

6. The fusion protein according to claim 1, wherein said linker is RADAAP (SEQ ID No: 12).

7. The fusion protein according to claim 1, wherein the allergen is P5 (SEQ ID No: 8) and the linker is RADAAP (SEQ ID No: 12).

8. The fusion protein according to claim 1, wherein the allergen is P1 (SEQ ID No: 4) and the linker is RADAAP (SEQ ID No: 12).

9. A method of treating shrimp allergy comprising administering to a subject a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, wherein the shrimp allergy is treated.

10. A vaccine composition comprising a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2.

11. Method for inhibiting and/or treating shrimp allergy, comprising administering to a mammal an effective amount of a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2 or a vaccine composition comprising a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2.

12. A kit comprising a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2 or a vaccine composition comprising a fusion protein comprising a first peptide and a second peptide linked together with a linker, wherein the first peptide is an allergen and the second peptide is a targeting unit and the second targeting unit peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, a container comprising said fusion protein or vaccine composition and optionally instructions for its use.

13. A method for preparing a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, comprising the steps of:

a) providing an isolated allergen peptide from shrimp tropomyosin Pan b 1 (SEQ ID No: 15) or a fragment thereof;

b) providing a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, c) fusing said isolated allergen peptide and said FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2 and said linker; and d) optionally isolating said fusion protein.

14. The method according to claim 13, wherein the fragments of shrimp tropomyosin Pan b 1 comprises the sequence according to any one of SEQ ID Nos: 4, 5, 6, 7, or 8.

15. The method according to claim 13, wherein the linker is RADAAP (SEQ ID No: 12).

16. A method for preparing a fusion protein comprising a first peptide and a second peptide linked together with a linker, wherein the first peptide is an allergen and the second peptide is a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, comprising the steps of:

a) providing a nucleic acid encoding an isolated allergen peptide from shrimp tropomyosin Pan b 1 (SEQ ID No: 15) or a fragment thereof;

b) providing a nucleic acid encoding a FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2, c) fusing said nucleic acid encoding said isolated allergen peptide and said nucleic acid encoding said FGL-2 C-terminal peptide selected from the group consisting of amino acids 23-122 of SEQ ID NO:1 and sequences with at least 95% identity to amino acids 23-122 of SEQ ID NO:1, and wherein said FGL-2 C-terminal peptide selected from the group consisting of amino acids 23-122 of SEQ ID NO:1 and sequences with at least 95% identity to amino acids 23-122 of SEQ ID NO:1 binds to human B-cells with a greater affinity than full-length FGL2 and a nucleic acid encoding said linker; and d) optionally isolating said fusion protein.

17. The method according to claim 16, wherein the fragments of shrimp tropomyosin Pan b 1 comprises the sequence according to any one of SEQ ID Nos: 4, 5, 6, 7, or 8.

18. The method according to claim 16, wherein the linker is RADAAP (SEQ ID No: 12).

* * * * *